US008419707B2

(12) United States Patent
Eckhoff et al.

(10) Patent No.: US 8,419,707 B2
(45) Date of Patent: Apr. 16, 2013

(54) DEVICE, SYSTEM, AND METHOD FOR TARGETED DELIVERY OF ANTI-INFLAMMATORY MEDICAMENTS TO A MAMMALIAN SUBJECT

(75) Inventors: Philip A. Eckhoff, Bellevue, WA (US); Roderick A. Hyde, Redmond, WA (US); Muriel Y. Ishikawa, Livermore, CA (US); Jordin T. Kare, Seattle, WA (US); Eric C. Leuthardt, St. Louis, MO (US); Dennis J. Rivet, Portsmouth, VA (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 352 days.

(21) Appl. No.: 12/660,111

(22) Filed: Feb. 19, 2010

(65) Prior Publication Data
US 2011/0118697 A1    May 19, 2011

Related U.S. Application Data

(63) Continuation of application No. 12/590,860, filed on Nov. 13, 2009, and a continuation-in-part of application No. 12/590,858, filed on Nov. 13, 2009, and a continuation-in-part of application No. 12/590,859, filed on Nov. 13, 2009, and a continuation-in-part of application No. 12/590,856, filed on Nov. 13, 2009, and a continuation-in-part of application No. 12/590,857, filed on Nov. 13, 2009.

(51) Int. Cl.
*A61M 31/00*    (2006.01)

(52) U.S. Cl.
USPC ............... 604/503; 604/20; 604/66; 604/67; 604/116; 604/890.1

(58) Field of Classification Search ............. 604/65–67, 604/890.1, 891.1, 116, 503
See application file for complete search history.

(56) References Cited

U.S. PATENT DOCUMENTS

| 5,130,257 A | 7/1992 | Baer et al. |
| 5,188,608 A | 2/1993 | Fritts |

(Continued)

OTHER PUBLICATIONS

Wermeling, Daniel P. et al.; Microneedles permit transdermal delivery of a skin-impermeant medication to humans; PNAS; Feb. 12, 2008; pp. 2058-2063; vol. 105; No. 6; The National Academy of Sciences of the USA.

(Continued)

*Primary Examiner* — Emily Schmidt
(74) *Attorney, Agent, or Firm* — Workman Nydegger

(57) ABSTRACT

A device, a system, or a method is described for treating a disease or a condition of one or more joints of articulating bone in a mammalian subject. The device provides one or more medicaments to one or more joints of the mammalian subject. A device is described that includes one or more substrates configured to contact one or more body contours in proximity to one or more joints of articulating bone of a mammalian subject; one or more sensors configured to detect one or more physiological conditions of the one or more joints; and one or more microjet applicators supported by the one or more substrates and configured to respond to the one or more sensors by injecting one or more medicaments to the one or more joint tissues of the mammalian subject.

29 Claims, 7 Drawing Sheets

U.S. PATENT DOCUMENTS

| | | | |
|---|---|---|---|
| 5,328,449 A * | 7/1994 | Andrews et al. ............. 602/42 | |
| 5,374,661 A | 12/1994 | Betlach, II | |
| 5,593,431 A | 1/1997 | Sheldon | |
| 5,753,266 A | 5/1998 | Youssefyeh et al. | |
| 5,895,386 A | 4/1999 | Odell et al. | |
| 6,078,842 A | 6/2000 | Gross et al. | |
| 6,143,329 A | 11/2000 | Kim | |
| 6,148,231 A | 11/2000 | Henley | |
| 6,379,324 B1 | 4/2002 | Gartstein et al. | |
| 6,560,483 B1 | 5/2003 | Kumar et al. | |
| 6,723,337 B1 | 4/2004 | Song et al. | |
| 6,743,211 B1 | 6/2004 | Prausnitz et al. | |
| 6,818,226 B2 | 11/2004 | Reed et al. | |
| 6,895,271 B2 | 5/2005 | Henley | |
| 6,955,819 B2 | 10/2005 | Zhang et al. | |
| 7,094,228 B2 | 8/2006 | Zhang et al. | |
| 7,128,711 B2 | 10/2006 | Medan et al. | |
| 7,244,447 B2 | 7/2007 | Hsu et al. | |
| 7,387,789 B2 | 6/2008 | Klose et al. | |
| 7,395,111 B2 | 7/2008 | Levin et al. | |
| 7,424,325 B2 | 9/2008 | Koller et al. | |
| 2001/0037104 A1 | 11/2001 | Zhang et al. | |
| 2002/0055702 A1 | 5/2002 | Atala et al. | |
| 2002/0099356 A1 | 7/2002 | Unger et al. | |
| 2002/0169411 A1 | 11/2002 | Sherman et al. | |
| 2003/0093057 A1 | 5/2003 | Zhang et al. | |
| 2004/0010207 A1 | 1/2004 | Flaherty et al. | |
| 2004/0141867 A1 | 7/2004 | Dreyer et al. | |
| 2004/0215135 A1 | 10/2004 | Sheldrake et al. | |
| 2004/0260234 A1 | 12/2004 | Srinivasan et al. | |
| 2005/0186141 A1 | 8/2005 | Gonda et al. | |
| 2005/0226921 A1 | 10/2005 | Kortzebom | |
| 2005/0226922 A1 | 10/2005 | Ameri et al. | |
| 2006/0020187 A1 | 1/2006 | Brister et al. | |
| 2006/0024358 A1 | 2/2006 | Santini, Jr. et al. | |
| 2006/0034902 A1 | 2/2006 | Cormier et al. | |
| 2006/0036209 A1 | 2/2006 | Subramony et al. | |
| 2006/0091139 A1 | 5/2006 | Grogan et al. | |
| 2006/0177494 A1 | 8/2006 | Cormier et al. | |
| 2007/0078414 A1 | 4/2007 | McAllister et al. | |
| 2007/0087901 A1 | 4/2007 | Brassil et al. | |
| 2007/0104766 A1 | 5/2007 | Wang et al. | |
| 2007/0136926 A1 | 6/2007 | Johnson et al. | |
| 2007/0141106 A1 | 6/2007 | Bonutti et al. | |
| 2007/0189978 A1 | 8/2007 | Zhang et al. | |
| 2007/0191758 A1 | 8/2007 | Hunter et al. | |
| 2007/0224252 A1 | 9/2007 | Trautman et al. | |
| 2007/0250134 A1 | 10/2007 | Miesel et al. | |
| 2007/0255111 A1 | 11/2007 | Miesel et al. | |
| 2007/0270738 A1 | 11/2007 | Wu et al. | |
| 2008/0021369 A1 | 1/2008 | Deem et al. | |
| 2008/0057534 A1 | 3/2008 | Martin et al. | |
| 2008/0091139 A1 | 4/2008 | Srinivasan et al. | |
| 2008/0125743 A1 | 5/2008 | Yuzhakov | |
| 2008/0171968 A1 | 7/2008 | Stout et al. | |
| 2008/0183144 A1 | 7/2008 | Trautman et al. | |
| 2008/0208107 A1 | 8/2008 | McRae et al. | |
| 2008/0226699 A1 | 9/2008 | Finnin et al. | |
| 2008/0269570 A1 | 10/2008 | Leung et al. | |
| 2008/0311167 A1 | 12/2008 | Oronsky et al. | |
| 2009/0005745 A1 | 1/2009 | Zhang et al. | |
| 2009/0093696 A1 | 4/2009 | Say et al. | |
| 2009/0099432 A1 | 4/2009 | Say et al. | |
| 2009/0118710 A1 | 5/2009 | Kortzeborn | |
| 2009/0137926 A1 | 5/2009 | Srinivasan et al. | |
| 2009/0155341 A1 | 6/2009 | Gavriely et al. | |
| 2009/0171192 A1 | 7/2009 | Patrick et al. | |
| 2009/0187167 A1 | 7/2009 | Sexton et al. | |
| 2010/0106076 A1 | 4/2010 | Nisato et al. | |
| 2010/0160894 A1 | 6/2010 | Julian et al. | |
| 2010/0178245 A1 | 7/2010 | Arnsdorf et al. | |
| 2010/0280446 A1 | 11/2010 | Kalpin | |
| 2011/0245580 A1 | 10/2011 | Leung et al. | |

OTHER PUBLICATIONS

Arora et al.; "Needle-free delivery of macromolecules across the skin by nanoliter-volume pulsed microjets"; PNAS; Mar. 13, 2007; pp. 4255-4260; vol. 104, No. 11.

Bruno et al.; "Naproxen kinetics in synovial fluid of patients with osteoarthritis"; Br. J. clin. Pharmac.; 1988; pp. 41-44; vol. 26.

Henry et al.; "Microfabricated Microneedles: A Novel Approach to Transdermal Drug Delivery"; Journal of Pharmaceutical Sciences; Aug. 1998; pp. 922-925; vol. 87, No. 8; American Chemical Society and American Pharmaceutical Association.

Huang et al.; "Low-noise wideband ultrasound detection using polymer microring resonators"; Applied Physics Letters; 2008; pp. 193509-1-193509-3; vol. 92; American Institute of Physics.

Karantonis et al.; "Implementation of a Real-Time Human Movement Classifier Using a Triaxial Accelerometer for Ambulatory Monitoring"; IEEE Transactions on Information Technology in Biomedicine; Jan. 2006; pp. 156-167; vol. 10, No. 1.

Kaushik et al.; "Lack of Pain Associated with Microfabricated Microneedles"; Anesth Analg; 2001; pp. 502-504; vol. 92; International Anesthesia Research Society.

Kyuki et al.; "Anti-Inflammatory Effect of Diclofenac-Sodium Ointment (Cream) in Topical Application"; Japan J. Pharmacol.; 1983; pp. 121-132; vol. 33.

Lee et al.; "Thixotropic property in pharmaceutical formulations"; Journal of Controlled Release; 2009; pp. 88-98; vol. 136; Elsevier B.V.

Levin, Galit; "Advances in Radio-Frequency Transdermal Drug Delivery"; Pharmaceutical Technology Drug Delivery; 2008; pp. s12-s19.

Mandahawi et al.; "Hand anthropometry survey for the Jordanian population"; International Journal of Industrial Ergonomics; 2008; pp. 966-976; vol. 38; Elsevier B.V.

Mason et al.; "Topical NSAIDs for chronic musculoskeletal pain: systematic review and meta-analysis"; BMC Musculoskeletal Disorders; Aug. 19, 2004; pp. 1-8; vol. 5, No. 28; BioMed Central Ltd.

McAllister et al.; "Microfabricated needles for transdermal delivery of macromolecules and nanoparticles: Fabrication methods and transport studies"; PNAS; Nov. 25, 2003; pp. 13755-13760; vol. 100, No. 24; The National Academy of Sciences of the USA.

Moore, R. Andrew; "Topical Nonsteroidal Antiinflammatory Drugs Are Effective in Osteoarthritis of the Knee"; The Journal of Rheumatology; 2004; pp. 1893-1894; vol. 31, No. 10; located at http://www.jrheum.com/subscribers/04/10/1893.html.

Özgüney, Işik; "An alternative topical treatment of osteoarthritis of the knee with cutaneous diclofenac solution"; Expert Opin. Pharmacother.; Jul. 2008; pp. 1805-1816; vol. 9, No. 10; Informa UK Ltd.

Sintov et al.; "Radiofrequency-driven skin microchanneling as a new way for electrically assisted transdermal delivery of hydrophilic drugs"; Journal of Controlled Release; 2003; pp. 311-320; vol. 89; Elsevier Science B.V.

"Arthritis;" A.D.A.M. Medical Encyclopedia; bearing a date of 2011, reviewed Feb. 14, 2011; pp. 1-4; A.D.A.M., Inc.

Mantovani, Alberto; "Pentraxins;" Encyclopedia of Molecular Medicine; bearing a date of 2002, published online Jan. 15, 2002; pp. 1-7; John Wiley & Sons, Inc.

Moskowitz, R. W. et al.; "Chapter 15: The Pharmacologic Treatment of Osteoarthrisis;" Osteoarthritis: Diagnosis and Medical/Surgical Management; bearing a date of 2007, Accessed online Apr. 16, 2012; p. 271-272; Lippincott Wiliams & Wilkins http://books.google.com/books?id=YfFj8Gbq5HOC&pg=PA272&Ipg=PA272&dq=nsaid+half+lif8+comparison+table&source=bl&0ts=6xgYcmKsuJ&s.

Schramm, L. L.; "Colloids;" Encyclopedia Of Polymer Science and Technology; bearing a date of 2004, published online Oct. 15, 2004; pp. 1-35; John Wiley & Sons, Inc.

* cited by examiner

DEVICE, SYSTEM, AND METHOD FOR TARGETED DELIVERY OF ANTI-INFLAMMATORY MEDICAMENTS TO A MAMMALIAN SUBJECT

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the United States Patent Office (USPTO) extra-statutory requirements, the present application is a CONTINUATION application of U.S. patent application Ser. No. 12/590,860 titled DEVICE, SYSTEM, AND METHOD FOR TARGETED DELIVERY OF ANTI-INFLAMMATORY MEDICAMENTS TO A MAMMALIAN SUBJECT, naming Philip A. Eckhoff, Roderick A. Hyde, Muriel Y. Ishikawa, Jordin T. Kare, Eric C. Leuthardt, Dennis J. Rivet, Elizabeth A. Sweeney, Lowell L. Wood, Jr. and Victoria Y. H. Wood as inventors, filed 13 Nov. 2009, which is co-pending, or is an application of which a co-pending application is entitled to the benefit of the filing date.

For purposes of the USPTO extra-statutory requirements, the present application constitutes a continuation-in-part of U.S. patent application Ser. No. 12/590,858, entitled DEVICE, SYSTEM, AND METHOD FOR TARGETED DELIVERY OF ANTI-INFLAMMATORY MEDICAMENTS TO A MAMMALIAN SUBJECT, naming Philip A. Eckhoff, Roderick A. Hyde, Muriel Y. Ishikawa, Jordin T. Kare, Eric C. Leuthardt, Dennis J. Rivet, Elizabeth A. Sweeney, Lowell L. Wood, Jr. and Victoria Y. H. Wood as inventors, filed 13 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,859, entitled DEVICE, SYSTEM, AND METHOD FOR TARGETED DELIVERY OF ANTI-INFLAMMATORY MEDICAMENTS TO A MAMMALIAN SUBJECT, naming Philip A. Eckhoff, Roderick A. Hyde, Muriel Y. Ishikawa, Jordin T. Kare, Eric C. Leuthardt, Dennis J. Rivet, Elizabeth A. Sweeney, Lowell L. Wood, Jr. and Victoria Y. H. Wood as inventors, filed 13 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,856, entitled DEVICE, SYSTEM, AND METHOD FOR TARGETED DELIVERY OF ANTI-INFLAMMATORY MEDICAMENTS TO A MAMMALIAN SUBJECT, naming Philip A. Eckhoff, Roderick A. Hyde, Muriel Y. Ishikawa, Jordin T. Kare, Eric C. Leuthardt, Dennis J. Rivet, Elizabeth A. Sweeney, Lowell L. Wood, Jr. and Victoria Y. H. Wood as inventors, filed 13 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,857, entitled DEVICE, SYSTEM, AND METHOD FOR TARGETED DELIVERY OF ANTI-INFLAMMATORY MEDICAMENTS TO A MAMMALIAN SUBJECT, naming Philip A. Eckhoff, Roderick A. Hyde, Muriel Y. Ishikawa, Jordin T. Kare, Eric C. Leuthardt, Dennis J. Rivet, Elizabeth A. Sweeney, Lowell L. Wood, Jr. and Victoria Y. H. Wood as inventors, filed 13 Nov. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A device is described for treating a disease or a condition of one or more joints of articulating bone in a mammalian subject. The device provides one or more medicaments to one or more joints of the mammalian subject. A device is described herein that includes one or more substrates configured to contact one or more body contours in proximity to one or more joints of articulating bone of a mammalian subject; one or more sensors configured to detect one or more physiological conditions of the one or more joints; and one or more microjet applicators supported by the one or more substrates and configured to respond to the one or more sensors by injecting one or more medicaments to the one or more joint tissues of the mammalian subject.

The one or more applicators can include one or more high speed microjets, e.g., nanoliter-volume pulsed microjets. The one or more substrates can include, but is not limited to, one or more patches or one or more sheaths. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace. The one or more substrates can be attached to the one or more body contours by a number of mechanisms including, but not limited to, glue, suction, suture, or hook.

The one or more applicators can further include, but are not limited to, a fluid displacement actuator configured as one or more piezoelectric actuators, one or more springs, one or more solenoids, one or more magnets, one or more motors, or one or more compressed gas actuators. In an aspect, the one or more applicators supported by the one or more substrates can be configured to respond to one or more sensors, wherein the one or more applicators are configured to inject the one or more medicaments to the one or more joint tissues of the mammalian subject.

In an aspect, the device can further include one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles. In an aspect, the one or more sensors, configured to detect one or more physiological conditions of the mammalian subject, can further be configured to detect tissue swelling, tissue pressure, tissue color, tissue temperature, environmental temperature, electrical property of tissue, optical property of tissue, perspiration, or presence of an analyte. The analyte can include an inflammatory marker, antibody, or cytokine. In an aspect, the device can further include one or more sensors configured to determine quality of location or quality of contact placement of the one or more sheaths on the one or more body contours.

In an aspect, the device can further include a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The controller can be configured to activate the one or more applicators based at least in part on an activity history of the mammalian subject. In a detailed aspect, the activity history can include joint movement or gait of the mammalian subject. The activity history can include, but is not limited to, frequency of use of the one or more joints, measured effort level of the one or more joints, inferred effort level of the one or more joints, or a preselected activity profile. The device can further include one or more sensors, wherein the controller is configured to respond to the one or more sensors. The one or more sensors can be configured to detect one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The device can further include a power source. The power source can include, but is not limited to, a motion-activated generator, solar cell, fuel cell, wireless source, battery or microbattery. The power source can be powered by motion of the body of the mammalian subject.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser.

The one or more sheaths can include a tourniquet configured to apply intermittent pressure in the region of the jointed area. The tourniquet can be configured to apply a constricting force thereby causing the one or more applicators to penetrate the stratum corneum of the skin of the mammalian subject.

The device can further include a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner. The one or more medicaments can include, but are not limited to, steroids, corticosteroids, analgesics, COX-2 inhibitors, or NSAIDs. The device can further include a pharmaceutical composition including the one or more medicaments in a thixotropic medium. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes injecting one or more medicaments to one or more joint tissues of a mammalian subject, wherein the injecting of the one or more medicaments is via a device including one or more substrates configured to contact one or more body contours in proximity to one or more joints of articulating bone of a mammalian subject; one or more sensors configured to detect one or more physiological conditions of the one or more joints; and one or more microjet applicators supported by the one or more substrates and configured to respond to the one or more sensors by injecting one or more medicaments to the one or more joint tissues of the mammalian subject.

The one or more applicators can include one or more high speed microjets, e.g., nanoliter-volume pulsed microjets. The one or more substrates can include, but is not limited to, one or more patches or one or more sheaths. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace.

The one or more applicators can further include, but are not limited to, a fluid displacement actuator configured as one or more piezoelectric actuators, one or more springs, one or more solenoids, one or more magnets, one or more motors, or one or more compressed gas actuators. In an aspect, the one or more applicators supported by the one or more substrates can be configured to respond to one or more sensors, wherein the one or more applicators are configured to inject the one or more medicaments to the one or more joint tissues of the mammalian subject.

In an aspect, the method can further include providing one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles. In an aspect, the one or more sensors, configured to detect one or more physiological conditions of the mammalian subject, can further be configured to detect tissue swelling, tissue pressure, tissue color, tissue temperature, environmental temperature, electrical property of tissue, optical property of tissue, perspiration, or presence of an analyte. The analyte can include an inflammatory marker, antibody, or cytokine. In an aspect, the method can further include providing one or more sensors configured to determine quality of location or quality of contact placement of the one or more sheaths on the one or more body contours.

In an aspect, the method can further include providing a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The controller can be configured to activate the one or more applicators based at least in part on an activity history of the mammalian subject. In a detailed aspect, the activity history can include joint movement or gait of the mammalian subject. The activity history can include, but is not limited to, frequency of use of the one or more joints, measured effort level of the one or more joints, inferred effort level of the one or more joints, or a preselected activity profile. The method can further include providing one or more sensors, wherein the controller is configured to respond to the one or more sensors. The one or more sensors can be configured to detect the one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The method can further include providing a power source. The power source can include, but is not limited to, a motion-activated generator, solar cell, fuel cell, wireless source, battery or microbattery. The power source can be powered by motion of the body of the mammalian subject.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser.

The one or more sheaths can include a tourniquet configured to apply intermittent pressure in the region of the jointed area. The tourniquet can be configured to apply a constricting force thereby causing the one or more applicators to penetrate the stratum corneum of the skin of the mammalian subject.

The method can further include providing a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner. The one or more medicaments can include, but are not limited to, steroids, corticosteroids, analgesics, COX-2 inhibitors, or NSAIDs. The method can further include providing a pharmaceutical composition including the one or more medicaments in a thixotropic medium. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes providing a device including one or more substrates configured to contact one or more body contours in proximity to one or more joints of articulating bone of a mammalian subject; one or more sensors configured to detect one or more physiological conditions of the one or more joints; and one or more microjet applicators supported by the one or more substrates and configured to respond to the one or more sensors by injecting one or more medicaments to the one or more joint tissues of the mammalian subject.

A system is described herein that includes at least one apparatus including one or more substrates configured to contact one or more body contours in proximity to one or more joints of articulating bone of a mammalian subject; one or more sensors configured to detect one or more physiological conditions of the one or more joints; and one or more microjet applicators supported by the one or more substrates and configured to respond to the one or more sensors by injecting one or more medicaments to the one or more joint tissues of the mammalian subject. The system can further include a recording device configured to collect data regarding one or more physiological conditions of the mammalian subject, and data regarding administration of the one or more medicaments to the one or more joint tissues of the mammalian subject. The data can include injection sites, medicament types, or medicament administration regimen to the mammalian subject. The data regarding the one or more physiological conditions of the mammalian subject can include movement of the contacted body contour, tissue swelling, tissue pressure, tissue color, tissue temperature, environmental temperature, electrical property of tissue, optical property of tissue, perspiration, or presence of an analyte.

A device is described herein that includes one or more sheaths configured to contact one or more body contours in proximity to one or more joints of articulating bone of a mammalian subject; and one or more microjet applicators supported by the one or more sheaths and configured to inject one or more medicaments to one or more joint tissues of the mammalian subject. The one or more applicators can include one or more high speed microjets, e.g., nanoliter-volume pulsed microjets. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace. The one or more joint tissues can include one or more of a fibrous capsule, subsynovium, synovial membrane, synovium, joint cavity, synovial fluid, articular cartilage, subchondral bone, or ligament. The one or more joints can include a synovial joint, cartilaginous joint, or fibrous joint. In an aspect, the one or more applicators supported by the one or more sheaths can be configured to respond to one or more sensors, wherein the one or more applicators are configured to inject the one or more medicaments to the one or more joint tissues of the mammalian subject.

In an aspect, the device can further include one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles.

In an aspect, the device can further include one or more sensors configured to detect one or more physiological conditions of the mammalian subject. The one or more sensors can be configured to detect tissue swelling, tissue pressure, tissue color, tissue temperature, environmental temperature, electrical property of tissue, optical property of tissue, perspiration, or presence of an analyte. The analyte can include an inflammatory marker, antibody, or cytokine.

In an aspect, the device can further include one or more sensors configured to determine quality of location or quality of contact placement of the one or more sheaths on the one or more body contours.

In an aspect, the device can further include a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The controller can be configured to activate the one or more applicators based at least in part on an activity history of the mammalian subject. In a detailed aspect, the activity history can include joint movement or gait of the mammalian subject. The activity history can include, but is not limited to, frequency of use of the one or more joints, measured effort level of the one or more joints, inferred effort level of the one or more joints, or a preselected activity profile. The device can further include one or more sensors, wherein the controller is configured to respond to the one or more sensors. The one or more sensors can be configured to detect one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The device can further include a power source. The power source can include, but is not limited to, a motion-activated generator, solar cell, fuel cell, wireless source, battery or microbattery. The power source can be powered by motion of the body of the mammalian subject.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser. The chemical permeation enhancer can include, but is not limited to, a dermal penetration enhancer including one or more esters including long chain alkyl para-aminobenzoate, long chain alkyl dimethyl-para-aminobenzoate, long chain alkyl cinnamate, long chain alkyl methoxycinnamate, long chain alkyl salicylate, octyl dimethyl-para-aminobenzoate, octyl para-methoxycinnamate, or octyl salicylate.

The one or more sheaths can include a tourniquet configured to apply intermittent pressure in the region of the jointed area. The tourniquet can be configured to apply a constricting force thereby causing the one or more applicators to penetrate the stratum corneum of the skin of the mammalian subject.

The device can further include a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner.

The one or more medicaments can include, but are not limited to, steroids, corticosteroids, analgesics, COX-2 inhibitors, or NSAIDs. The NSAID include, but is not limited to, acemetacin, arntolmetin, azapropazone, benorilate, benoxaprofen, benzydamine hydrochloride, bromfenal, bufexamac, butibufen, carprofen, celecoxib, choline salicylate, diclofenac dipyone, droxicam, etodolac, etofenamate, etoricoxib, felbinac, fentiazac, floctafenine, ibuprofen, indoprofen, isoxicam, lomoxicam, loxoprofen, licofelone, fepradinol, magnesium salicylate, meclofenamic acid, meloxicam, morniflumate, niflumic acid, nimesulide, oxaprozen, piketoprofen, priazolac, pirprofen, propyphenazone, proquazone, rofecoxib, salalate, sodium salicylate, sodium thiosalicylate, suprofen, tenidap, tiaprofenic acid, trolamine salicylate, zomepirac, aclofenac, aloxiprin, naproxen, aproxen, aspirin, diflunisal, fenoprofen, indomethacin, mefenamic acid, piroxicam, phenylbutazone, salicylamide, salicylic acid, sulindac, desoxysulindac, tenoxicam, tramadol, ketoralac, clonixin, fenbufen, benzydamine hydrochloride, meclofenamic acid, flufenamic acid, or tolmetin. The device can further include a pharmaceutical composition including the one or more medicaments in a thixotropic medium.

The device can further include, but is not limited to, one or more microneedles, one or more microfine lances, one or more microfine cannulas, one or more microprojections, or one or more electrodes, supported by the one or more sheaths and configured to inject the one or more medicaments to the one or more joint tissues of the mammalian subject. The one or more applicators can include electrodes on microprojections configured to apply electrical energy to skin of the mammalian subject. The electrodes on microprojections can provide ablation of stratum corneum in an area beneath the electrodes thereby generating a plurality of hydrophilic microchannels in the skin of the mammalian subject. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes injecting one or more medicaments to one or more joint tissues of a mammalian subject, wherein the injecting of the one or more medicaments is via a device including one or more sheaths configured to contact one or more body contours in proximity to one or more joints of articulating bone of the mammalian subject; and one or more microjet applicators supported by the one or more sheaths and configured to inject one or more medicaments to one or more joint tissues of the mammalian subject.

The one or more applicators can include one or more high speed microjets, e.g., nanoliter-volume pulsed microjets. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace. The one or more joint tissues can include one or more of a fibrous capsule, subsynovium, synovial membrane, synovium, joint cavity, synovial fluid, articular cartilage, subchondral bone, or ligament. The one or more joints can include a synovial joint, cartilaginous joint, or fibrous joint. In an aspect, the one or more applicators supported by the one or more sheaths can be configured to respond to one or more sensors, wherein the one or more applicators are configured to inject the one or more medicaments to the one or more joint tissues of the mammalian subject.

In an aspect, the method can further include providing one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles.

In an aspect, the method can further include providing one or more sensors configured to detect one or more physiological conditions of the mammalian subject. The one or more sensors can be configured to detect tissue swelling, tissue pressure, tissue color, tissue temperature, environmental temperature, electrical property of tissue, optical property of tissue, perspiration, or presence of an analyte. The analyte can include an inflammatory marker, antibody, or cytokine.

In an aspect, the method can further include providing one or more sensors configured to determine quality of location or quality of contact placement of the one or more sheaths on the one or more body contours. In an aspect, the method can further providing include a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The method can further include providing one or more sensors, wherein the controller is configured to respond to the one or more sensors. The one or more sensors can be configured to detect one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser.

The one or more sheaths can include a tourniquet configured to apply intermittent pressure in the region of the jointed area. The tourniquet can be configured to apply a constricting force thereby causing the one or more applicators to penetrate the stratum corneum of the skin of the mammalian subject.

The method can further include providing a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner.

The one or more medicaments can include, but are not limited to, steroids, corticosteroids, analgesics, COX-2 inhibitors, or NSAIDs. The method can further include a pharmaceutical composition including the one or more medicaments in a thixotropic medium. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes providing a device including one or more sheaths configured to contact one or more body contours in proximity to one or more joints of articulating bone of the mammalian subject; and one or more microjet applicators supported by the one or more sheaths and configured to inject one or more medicaments to one or more joint tissues of the mammalian subject.

A system is described herein that includes at least one apparatus including one or more sheaths configured to contact one or more body contours in proximity to one or more joints of articulating bone of a mammalian subject; and one or more microjet applicators supported by the one or more sheaths and configured to inject one or more medicaments to one or more joint tissues of the mammalian subject.

A device is described herein that includes one or more substrates configured to contact one or more body contours in proximity to one or more joints of articulating bone of a mammalian subject; one or more sensors configured to monitor movement of the one or more body contours; and one or more applicators supported by the one or more substrates and configured to respond to the movement of the one or more body contours by injecting one or more medicaments to the one or more joint tissues of the mammalian subject. The one or more substrates can include, but is not limited to, one or more patches or one or more sheaths. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace. The one or more substrates can be attached to the one or more body contours by a number of mechanisms including, but not limited to, glue, suction, suture, or hook. The one or more applicators can include one or more high speed microjets, one or more microneedles, one or more microfine lances, one or more microfine cannulas, one or more microprojections, or one or more electrodes, wherein the one or more applicators can be supported by the one or more sheaths and can be configured to inject the one or more medicaments to the one or more joint tissues of the mammalian subject. The one or more applicators can include one or more high speed microjets, e.g., nanoliter-volume pulsed microjets. The one or more applicators can further include, but are not limited to, a fluid displacement actuator configured as one or more piezoelectric actuators, one or more springs, one or more solenoids, one or more magnets, one or more motors, or one or more compressed gas actuators. The one or more applicators includes electrodes on microprojections configured to apply electrical energy to skin of the mammalian subject. The electrodes on microprojections can provide ablation of stratum corneum in an area beneath the electrodes thereby generating a plurality of hydrophilic microchannels in the skin of the mammalian subject. In an aspect, the one or more microneedles, the one or more microfine lances, the one or more microfine cannulas, or the one or more microprojections can contact the one or more joint tissues of the mammalian subject. In an aspect, the one or more applicators supported by the one or more substrates can be configured to respond to one or more sensors, wherein the one or more applicators are configured to inject the one or more medicaments to the one or more joint tissues of the mammalian subject. The one or more joint tissues can include one or more of a fibrous capsule, subsynovium, synovial membrane, synovium, joint cavity, synovial fluid, articular cartilage, subchondral bone, or ligament. The one or more joints can include a synovial joint, cartilaginous joint, or fibrous joint.

In an aspect, the device can further include one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles.

In an aspect, the device can further include one or more sensors configured to detect one or more physiological conditions of the mammalian subject. The one or more sensors can be configured to detect tissue swelling, tissue pressure, tissue color, tissue temperature, environmental temperature, electrical property of tissue, optical property of tissue, perspiration, or presence of an analyte. The analyte can include an inflammatory marker, antibody, or cytokine.

In an aspect, the device can further include one or more sensors configured to determine quality of location or quality of contact placement of the one or more sheaths on the one or more body contours.

In an aspect, the device can further include a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The controller can be configured to activate the one or more applicators based at least in part on an activity history of the mammalian subject. In a detailed aspect, the activity history can include joint movement or gait of the mammalian subject. The activity history can include, but is not limited to, frequency of use of the one or more joints, measured effort level of the one or more joints, inferred effort level of the one or more joints, or a preselected activity profile. The controller can be configured to respond to the one or more sensors. The one or more sensors can be configured to detect one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The device can further include a power source. The power source can include, but is not limited to, a motion-activated generator, solar cell, fuel cell, wireless source, battery or microbattery. The power source can be powered by motion of the body of the mammalian subject.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser.

The one or more sheaths can include a tourniquet configured to apply intermittent pressure in the region of the jointed area. The tourniquet can be configured to apply a constricting force thereby causing the one or more applicators to penetrate the stratum corneum of the skin of the mammalian subject.

The device can further include a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner. The one or more medicaments can include, but are not limited to, steroids, corticosteroids, analgesics, COX-2 inhibitors, or NSAIDs. The device can further include a pharmaceutical composition including the one or more medicaments in a thixotropic medium. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes injecting one or more medicaments to one or more joint tissues of a mammalian subject, wherein the injecting of the one or more medicaments is via a device including one or more substrates configured to contact one or more body contours in proximity to one or more joints of articulating bone of a mammalian subject; one or more sensors configured to monitor movement of the one or more body contours; and one or more applicators supported by the one or more substrates and configured to respond to the movement of the one or more body contours by injecting one or more medicaments to the one or more joint tissues of the mammalian subject. The one or more substrates can include, but is not limited to, one or more patches or one or more sheaths. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace. The one or more applicators can include one or more high speed microjets, one or more microneedles, one or more microfine lances, one or more microfine cannulas, one or more microprojections, or one or more electrodes, wherein the one or more applicators can be supported by the one or more sheaths and can be configured to inject the one or more medicaments to the one or more joint tissues of the mammalian subject. The one or more applicators can include one or more high speed microjets, e.g., nanoliter-volume pulsed microjets. The one or more applicators can further include, but are not limited to, a fluid displacement actuator configured as one or more piezoelectric actuators, one or more springs, one or more solenoids, one or more magnets, one or more motors, or one or more compressed gas actuators. The one or more applicators includes electrodes on microprojections configured to apply electrical energy to skin of the mammalian subject. The electrodes on microprojections can provide ablation of stratum corneum in an area beneath the electrodes thereby generating a plurality of hydrophilic microchannels in the skin of the mammalian subject. In an aspect, the one or more microneedles, the one or more microfine lances, the one or more microfine cannulas, or the one or more microprojections can contact the one or more joint tissues of the mammalian subject. In an aspect, the one or more applicators supported by the one or more substrates can be configured to respond to one or more sensors, wherein the one or more applicators are configured to inject the one or more medicaments to the one or more joint tissues of the mammalian subject. The one or more joint tissues can include one or more of a fibrous capsule, subsynovium, synovial membrane, synovium, joint cavity, synovial fluid, articular cartilage, subchondral bone, or ligament. The one or more joints can include a synovial joint, cartilaginous joint, or fibrous joint.

In an aspect, the method can further include providing one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles.

In an aspect, the method can further include providing one or more sensors configured to detect one or more physiological conditions of the mammalian subject. The one or more sensors can be configured to detect tissue swelling, tissue pressure, tissue color, tissue temperature, environmental temperature, electrical property of tissue, optical property of tissue, perspiration, or presence of an analyte. The analyte can include an inflammatory marker, antibody, or cytokine.

In an aspect, the method can further include providing one or more sensors configured to determine quality of location or quality of contact placement of the one or more sheaths on the one or more body contours.

In an aspect, the method can further include providing a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The controller can be configured to activate the one or more applicators based at least in part on an activity history of the mammalian subject. In a detailed aspect, the activity history can include joint movement or gait of the mammalian subject. The activity history can include, but is not limited to, frequency of use of the one or more joints, measured effort level of the one or more joints, inferred effort level of the one or more joints, or a preselected activity profile. The controller can be configured to respond to the one or more sensors. The one or more sensors can be configured to detect one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The method can further include providing a power source. The power source can include, but is not limited to, a motion-activated generator, solar cell, fuel cell, wireless source, battery or microbattery. The power source can be powered by motion of the body of the mammalian subject.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser.

The one or more sheaths can include a tourniquet configured to apply intermittent pressure in the region of the jointed area. The tourniquet can be configured to apply a constricting force thereby causing the one or more applicators to penetrate the stratum corneum of the skin of the mammalian subject.

The method can further include providing a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner. The one or more medicaments can include, but are not limited to, steroids, corticosteroids, analgesics, COX-2 inhibitors, or NSAIDs. The method can further include providing a pharmaceutical composition including the one or more medicaments in a thixotropic medium. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes providing a device including one or more substrates configured to contact one or more body contours in proximity to one or more joints of articulating bone of a mammalian subject; one or more sensors configured to monitor movement of the one or more body contours; and one or more applicators supported by the one or more substrates and configured to respond to the movement of the one or more body contours by injecting one or more medicaments to the one or more joint tissues of the mammalian subject.

A system is described herein that includes at least one apparatus including one or more substrates configured to contact one or more body contours in proximity to one or more joints of articulating bone of a mammalian subject; one or more sensors configured to monitor movement of the one or more body contours; and one or more applicators supported by the one or more substrates and configured to respond to the movement of the one or more body contours by injecting one or more medicaments to the one or more joint tissues of the mammalian subject.

A device is described herein that includes one or more sheaths configured to contact one or more body contours in proximity to one or more joints of articulating bone of a mammalian subject; one or more sensors configured to detect one or more physiological conditions of the one or more joints; and one or more applicators supported by the one or more sheaths and configured to respond to the one or more sensors by injecting one or more medicaments to one or more joint tissues of the mammalian subject. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace.

The one or more applicators can include one or more high speed microjets, one or more microneedles, one or more microfine lances, one or more microfine cannulas, one or more microprojections, or one or more electrodes, wherein the one or more applicators can be supported by the one or more sheaths and can be configured to inject the one or more medicaments to the one or more joint tissues of the mammalian subject. The one or more applicators can include one or more high speed microjets, e.g., nanoliter-volume pulsed microjets. The one or more applicators can further include, but are not limited to, a fluid displacement actuator configured as one or more piezoelectric actuators, one or more springs, one or more solenoids, one or more magnets, one or more motors, or one or more compressed gas actuators. The one or more applicators includes electrodes on microprojections configured to apply electrical energy to skin of the mammalian subject. The electrodes on microprojections can provide ablation of stratum corneum in an area beneath the electrodes thereby generating a plurality of hydrophilic microchannels in the skin of the mammalian subject. In an aspect, the one or more microneedles, the one or more microfine lances, the one or more microfine cannulas, or the one or more microprojections can contact the one or more joint tissues of the mammalian subject. In an aspect, the one or more applicators supported by the one or more sheaths can be configured to respond to one or more sensors, wherein the one or more applicators are configured to inject the one or more medicaments to the one or more joint tissues of the mammalian subject.

In an aspect, the device can further include one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles. In an aspect, the one or more sensors, configured to detect one or more physiological conditions of the mammalian subject, can further be configured to detect tissue swelling, tissue pressure, tissue color, tissue temperature, environmental temperature, electrical property of tissue, optical property of tissue, perspiration, or presence of an analyte. The analyte can include an inflammatory marker, antibody, or cytokine. In an aspect, the device can further include one or more sensors configured to determine quality of location or quality of contact placement of the one or more sheaths on the one or more body contours.

In an aspect, the device can further include a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The controller can be configured to activate the one or more applicators based at least in part on an activity history of the mammalian subject. In a detailed aspect, the activity history can include joint movement or gait of the mammalian subject. The activity history can include, but is not limited to, frequency of use of the one or more joints, measured effort level of the one or more joints, inferred effort level of the one or more joints, or a preselected activity profile. The device can further include one or more sensors, wherein the controller is configured to respond to the one or more sensors. The one or more sensors can be configured to detect one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The device can further include a power source. The power source can include, but is not limited to, a motion-activated generator, solar cell, fuel cell, wireless source, battery or microbattery. The power source can be powered by motion of the body of the mammalian subject.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser.

The one or more sheaths can include a tourniquet configured to apply intermittent pressure in the region of the jointed area. The tourniquet can be configured to apply a constricting force thereby causing the one or more applicators to penetrate the stratum corneum of the skin of the mammalian subject.

The device can further include a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner. The one or more medicaments can include, but are not limited to, steroids, corticosteroids, analgesics, COX-2 inhibitors, or NSAIDs. The device can further include a pharmaceutical composition including the one or more medicaments in a thixotropic medium. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes injecting one or more medicaments to one or more joint tissues of a mammalian subject, wherein the injecting of the one or more medicaments is via a device including one or more sheaths configured to contact one or more body contours in proximity to one or more joints of articulating bone of a mammalian subject; one or more sensors configured to detect one or more physiological conditions of the one or more joints; and one or more applicators supported by the one or more sheaths and configured to respond to the one or more sensors by injecting one or more medicaments to one or more joint tissues of the mammalian subject. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace.

The one or more applicators can include one or more high speed microjets, one or more microneedles, one or more microfine lances, one or more microfine cannulas, one or more microprojections, or one or more electrodes, wherein the one or more applicators can be supported by the one or more sheaths and can be configured to inject the one or more medicaments to the one or more joint tissues of the mammalian subject. The one or more applicators can include one or more high speed microjets, e.g., nanoliter-volume pulsed microjets. The one or more applicators can further include, but are not limited to, a fluid displacement actuator configured as one or more piezoelectric actuators, one or more springs, one or more solenoids, one or more magnets, one or more motors, or one or more compressed gas actuators. The one or more applicators includes electrodes on microprojections configured to apply electrical energy to skin of the mammalian subject. The electrodes on microprojections can provide ablation of stratum corneum in an area beneath the electrodes thereby generating a plurality of hydrophilic microchannels in the skin of the mammalian subject. In an aspect, the one or more microneedles, the one or more microfine lances, the one or more microfine cannulas, or the one or more microprojections can contact the one or more joint tissues of the mammalian subject. In an aspect, the one or more applicators supported by the one or more sheaths can be configured to respond to one or more sensors, wherein the one or more applicators are configured to inject the one or more medicaments to the one or more joint tissues of the mammalian subject.

In an aspect, the method can further include providing one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles. In an aspect, the one or more sensors, configured to detect one or more physiological conditions of the mammalian subject, can further be configured to detect tissue swelling, tissue pressure, tissue color, tissue temperature, environmental temperature, electrical property of tissue, optical property of tissue, perspiration, or presence of an analyte. The analyte can include an inflammatory marker, antibody, or cytokine. In an aspect, the method can further include providing one or more sensors configured to determine quality of location or quality of contact placement of the one or more sheaths on the one or more body contours.

In an aspect, the method can further include providing a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The controller can be configured to activate the one or more applicators based at least in part on an activity history of the mammalian subject. In a detailed aspect, the activity history can include joint movement or gait of the mammalian subject. The activity history can include, but is not limited to, frequency of use of the one or more joints, measured effort level of the one or more joints, inferred effort level of the one or more joints, or a preselected activity profile. The method can further include providing one or more sensors, wherein the controller is configured to respond to the one or more sensors. The one or more sensors can be configured to detect one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The method can further include providing a power source. The power source can include, but is not limited to, a motion-activated generator, solar cell, fuel cell, wireless source, battery or microbattery. The power source can be powered by motion of the body of the mammalian subject.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser.

The one or more sheaths can include a tourniquet configured to apply intermittent pressure in the region of the jointed area. The tourniquet can be configured to apply a constricting force thereby causing the one or more applicators to penetrate the stratum corneum of the skin of the mammalian subject.

The method can further include providing a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner. The one or more medicaments can include, but are not limited to, steroids, corticosteroids, analgesics, COX-2 inhibitors, or NSAIDs. The method can further include providing a pharmaceutical composition including the one or more medicaments in a thixotropic medium. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes providing a device including one or more sheaths configured to contact one or more body contours in proximity to one or more joints of articulating bone of a mammalian subject; one or more sensors configured to detect one or more physiological conditions of the one or more joints; and one or more applicators supported by the one or more sheaths and configured to respond to the one or more sensors by injecting one or more medicaments to one or more joint tissues of the mammalian subject. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace.

A system is described herein that includes at least one apparatus including one or more sheaths configured to contact one or more body contours in proximity to one or more joints of articulating bone of a mammalian subject; one or more sensors configured to detect one or more physiological conditions of the one or more joints; and one or more applicators supported by the one or more sheaths and configured to respond to the one or more sensors by injecting one or more medicaments to the one or more joint tissues of the mammalian subject.

A device is described herein that includes an enclosure including one or more sensors, a controller, and one or more applicators configured to surround one or more joints of articulating bone of a mammalian subject, wherein the one or more sensors are configured to detect one or more physiological conditions of the one or more joints of the mammalian subject, and the controller, configured to communicate with the one or more sensors, is configured to activate the one or more applicators, and wherein the one or more applicators are configured to inject one or more medicaments to one or more joint tissues of the mammalian subject.

The one or more sensors can be configured to detect a physiological condition including, but not limited to, tissue swelling, tissue pressure, tissue color, tissue temperature, environmental temperature, electrical property of tissue, optical property of tissue, perspiration, or presence of an analyte. The analyte can include an inflammatory marker, antibody, or cytokine. The one or more applicators can include one or more high speed microjets, one or more microneedles, one or more microfine lances, one or more microfine cannulas, one or more microprojections, or one or more electrodes, wherein the one or more applicators can be supported by the one or more sheaths and can be configured to inject the one or more medicaments to the one or more joint tissues of the mammalian subject. The one or more applicators can include one or more high speed microjets, e.g., nanoliter-volume pulsed microjets. The one or more applicators can further include, but are not limited to, a fluid displacement actuator configured as one or more piezoelectric actuators, one or more springs, one or more solenoids, one or more magnets, one or more motors, or one or more compressed gas actuators. The one or more applicators includes electrodes on microprojections configured to apply electrical energy to skin of the mammalian subject. The electrodes on microprojections can provide ablation of stratum corneum in an area beneath the electrodes thereby generating a plurality of hydrophilic microchannels in the skin of the mammalian subject. In an aspect, the one or more microneedles, the one or more microfine lances, the one or more microfine cannulas, or the one or more microprojections can contact the one or more joint tissues of the mammalian subject. In an aspect, the one or more applicators can be configured to respond to one or more sensors, wherein the one or more applicators are configured to inject the one or more medicaments to the one or more joint tissues of the mammalian subject. The one or more joint tissues can include one or more of a fibrous capsule, subsynovium, synovial membrane, synovium, joint cavity, synovial fluid, articular cartilage, subchondral bone, or ligament. The one or more joints can include a synovial joint, cartilaginous joint, or fibrous joint.

In an aspect, the device can further include one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles.

In an aspect, the device can further include a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The controller can be configured to activate the one or more applicators based at least in part on an activity history of the mammalian subject. In a detailed aspect, the activity history can include joint movement or gait of the mammalian subject. The activity history can include, but is not limited to, frequency of use of the one or more joints, measured effort level of the one or more joints, inferred effort level of the one or more joints, or a preselected activity profile. The controller can be configured to respond to the one or more sensors. The one or more sensors can be configured to detect one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The device can further include a power source. The power source can include, but is not limited to, a motion-activated generator, solar cell, fuel cell, wireless source, battery, microbattery, or wired source.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser. The chemical permeation enhancer can include, but is not limited to, a dermal penetration enhancer including one or more esters including long chain alkyl para-aminobenzoate, long chain alkyl dimethyl-para-aminobenzoate, long chain alkyl cinnamate, long chain alkyl methoxycinnamate, long chain alkyl salicylate, octyl dimethyl-para-aminobenzoate, octyl para-methoxycinnamate, or octyl salicylate The enclosure can include a tourniquet configured to apply intermittent pressure in the region of the jointed area. The tourniquet can be configured to apply a constricting force thereby causing the one or more applicators to penetrate the stratum corneum of the skin of the mammalian subject.

The device can further include a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner. The one or more medicaments can include, but are not limited to, steroids, corticosteroids, analgesics, COX-2 inhibitors, or NSAIDs. The device can further include a pharmaceutical composition including the one or more medicaments in a thixotropic medium. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes injecting one or more medicaments to one or more joint tissues of a mammalian subject, wherein the injecting of the one or more medicaments is via a device including an enclosure including one or more sensors, a controller, and one or more applicators configured to surround one or more joints of articulating bone of a mammalian subject, wherein the one or more sensors are configured to detect one or more physiological conditions of the one or more joints of the mammalian subject, and the controller, configured to communicate with the one or more sensors, is configured to activate the one or more applicators, and wherein the one or more applicators are configured to inject one or more medicaments to one or more joint tissues of the mammalian subject.

The one or more sensors can be configured to detect a physiological condition including, but not limited to, tissue swelling, tissue pressure, tissue color, tissue temperature, environmental temperature, electrical property of tissue, optical property of tissue, perspiration, or presence of an analyte. The analyte can include an inflammatory marker, antibody, or cytokine. The one or more applicators can include one or more high speed microjets, one or more microneedles, one or more microfine lances, one or more microfine cannulas, one or more microprojections, or one or more electrodes, wherein the one or more applicators can be supported by the one or more sheaths and can be configured to inject the one or more medicaments to the one or more joint tissues of the mammalian subject. The one or more applicators can include one or more high speed microjets, e.g., nanoliter-volume pulsed microjets. The one or more applicators can further include, but are not limited to, a fluid displacement actuator configured as one or more piezoelectric actuators, one or more springs, one or more solenoids, one or more magnets, one or more motors, or one or more compressed gas actuators. The one or more applicators includes electrodes on microprojections configured to apply electrical energy to skin of the mammalian subject. The electrodes on microprojections can provide ablation of stratum corneum in an area beneath the electrodes thereby generating a plurality of hydrophilic microchannels in the skin of the mammalian subject. In an aspect, the one or more microneedles, the one or more microfine lances, the one or more microfine cannulas, or the one or more microprojections can contact the one or more joint tissues of the mammalian subject. In an aspect, the one or more applicators can be configured to respond to one or more sensors, wherein the one or more applicators are configured to inject the one or more medicaments to the one or more joint tissues of the mammalian subject. The one or more joint tissues can include one or more of a fibrous capsule, subsynovium, synovial membrane, synovium, joint cavity, synovial fluid, articular cartilage, subchondral bone, or ligament. The one or more joints can include a synovial joint, cartilaginous joint, or fibrous joint.

In an aspect, the method can further include providing one or more sensors configured to detect movement of the one or more body contours. The one or more sensors can be configured to monitor joint movement, body movement, or gait of the mammalian subject. The one or more sensors can be configured to monitor posture of the mammalian subject. The one or more sensors can be configured to monitor frequency of joint use or level of effort used by the one or more joints. In a detailed aspect, the level of effort used by the one or more joints includes measured effort or inferred effort. The one or more sensors can be configured to monitor a preselected set of activity profiles.

In an aspect, the providing can further include providing a controller configured to control release of the one or more medicaments from the one or more applicators. The controller can be configured to control a timed-release dosage of the one or more medicaments. The controller can be configured to report quantity and frequency of dosage of the one or more medicaments. The controller can be configured to control a maximum dosage of the one or more medicaments for a time period. The controller can be configured to activate the one or more applicators based at least in part on an activity history of the mammalian subject. In a detailed aspect, the activity history can include joint movement or gait of the mammalian subject. The activity history can include, but is not limited to, frequency of use of the one or more joints, measured effort level of the one or more joints, inferred effort level of the one or more joints, or a preselected activity profile. The controller can be configured to respond to the one or more sensors. The one or more sensors can be configured to detect one or more conditions at one or more of the one or more joints and the controller is configured to control release of the one or more medicaments at others of the one or more joints of the mammalian subject. In an aspect, the one or more sensors are configured to detect one or more physiological conditions of the mammalian subject. In a further aspect, the one or more sensors are configured to detect movement of the one or more body contours.

The method can further include providing a power source. The power source can include, but is not limited to, a motion-activated generator, solar cell, fuel cell, wireless source, battery, microbattery, or wired source.

The one or more applicators can further include, but are not limited to, tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser. The chemical permeation enhancer can include, but is not limited to, a dermal penetration enhancer including one or more esters including long chain alkyl para-aminobenzoate, long chain alkyl dimethyl-para-aminobenzoate, long chain alkyl cinnamate, long chain alkyl methoxycinnamate, long chain alkyl salicylate, octyl dimethyl-para-aminobenzoate, octyl para-methoxycinnamate, or octyl salicylate The enclosure can include a tourniquet configured to apply intermittent pressure in the region of the jointed area. The tourniquet can be configured to apply a constricting force thereby causing the one or more applicators to penetrate the stratum corneum of the skin of the mammalian subject.

The method can further include providing a component for transient mechanical/electrical acceleration of the one or more medicaments from the high speed microjets. The component for transient mechanical/electrical acceleration can include a fluid displacement actuator configured as one or more piezoelectric actuators, one or more springs, one or more solenoids, one or more magnets, one or more motors, or one or more compressed gas actuators. The component for mechanical/electrical acceleration is configured to apply concentration gradients of the one or more medicaments in a time-dependent manner. The one or more medicaments can include, but are not limited to, steroids, corticosteroids, analgesics, COX-2 inhibitors, or NSAIDs. The device can further include a pharmaceutical composition including the one or more medicaments in a thixotropic medium. The one or more applicators can be configured to apply the one or more medicaments in a time-dependent manner. The one or more applicators can be configured to apply the one or more medicaments in concentration gradients in the time-dependent manner. The one or more medicaments can be configured to have a short effective half-life. The one or more medicaments can be configured to have a long effective half-life.

A method is described herein that includes providing a device including an enclosure including one or more sensors, a controller, and one or more applicators configured to surround one or more joints of articulating bone of a mammalian subject, wherein the one or more sensors are configured to detect one or more physiological conditions of the one or more joints of the mammalian subject, and the controller, configured to communicate with the one or more sensors, is configured to activate the one or more applicators, and wherein the one or more applicators are configured to inject one or more medicaments to one or more joint tissues of the mammalian subject.

A system is described herein that includes at least one apparatus including an enclosure including one or more sensors, a controller, and one or more applicators configured to surround one or more joints of articulating bone of a mammalian subject, wherein the one or more sensors are configured to detect one or more physiological conditions of the one or more joints of the mammalian subject, and the controller, configured to communicate with the one or more sensors, is configured to activate the one or more applicators, and wherein the one or more applicators are configured to inject one or more medicaments to one or more joint tissues of the mammalian subject.

The foregoing summary is illustrative only and is not intended to be in any way limiting. In addition to the illustrative aspects, embodiments, and features described above, an aspect, embodiments, and features will become apparent by reference to the drawings and the following detailed description.

DETAILED DESCRIPTION

Figure 1A:
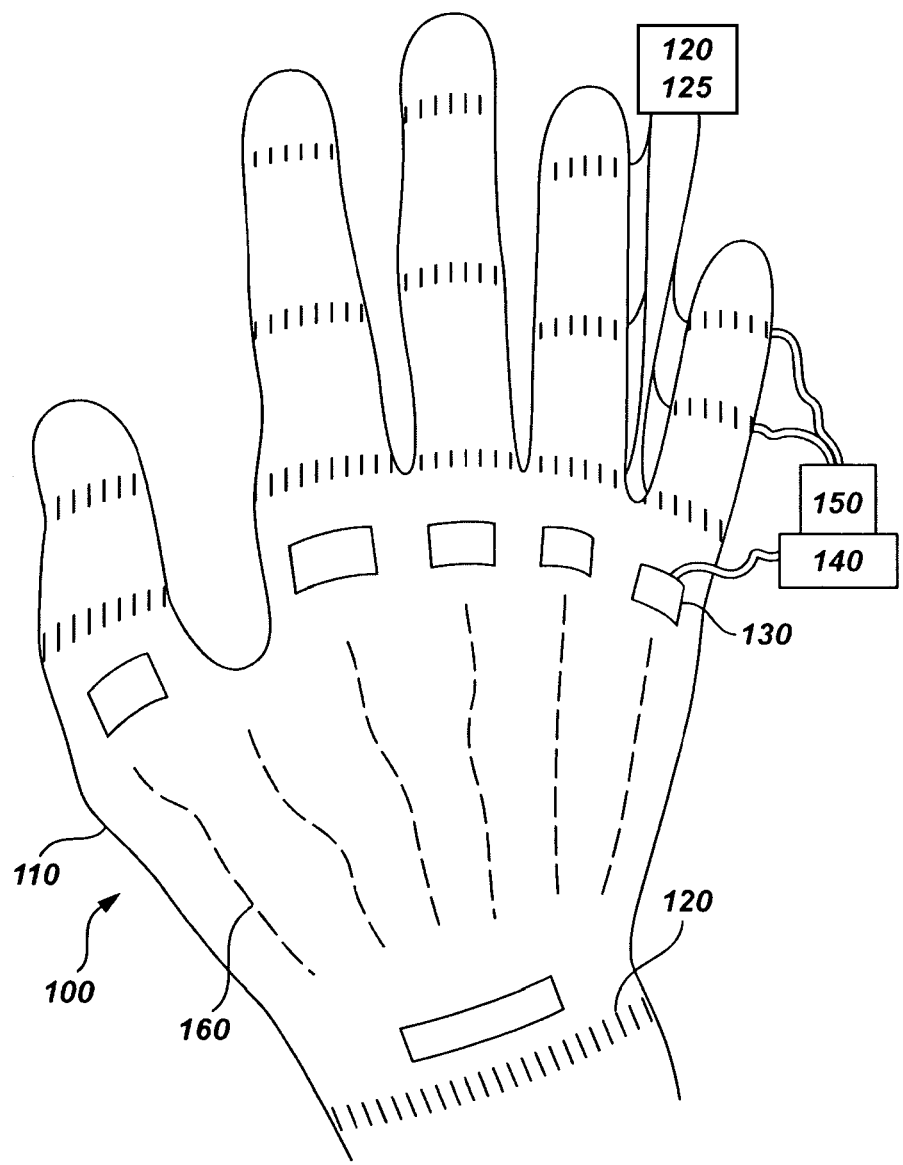
FIGS. 1A-1C depict a diagrammatic view of an aspect of a device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

A device is described for treating a disease or a condition of one or more joints of articulating bone in a mammalian subject. The device provides one or more medicaments to one or more joints of the mammalian subject. A device is described herein that includes one or more substrates configured to contact one or more body contours in proximity to one or more joints of articulating bone of a mammalian subject; one or more sensors configured to detect one or more physiological conditions of the one or more joints; and one or more microjet applicators supported by the one or more substrates and configured to respond to the one or more sensors by injecting one or more medicaments to the one or more joint tissues of the mammalian subject. The one or more applicators can include one or more high speed microjets, e.g., nanoliter-volume pulsed microjets. The one or more substrates can include, but is not limited to, one or more patches or one or more sheaths. The one or more sheaths can include a sleeve-shaped article of clothing or a sleeve-shaped body covering. In an aspect, the one or more sheaths can include shirt sleeve, pant, leg covering, glove, stocking, bandage-like covering, brace, knee brace, elbow brace, ankle brace, foot brace, hand brace, or spinal brace. The sheath can include an article of clothing including, but not limited to, a partial or full article of clothing, e.g., a partial glove that covers two or more fingers or a full glove that covers a hand; a ¾ length sleeve, or a full length sleeve. The one or more substrates can be attached to the one or more body contours by a number of mechanisms including, but not limited to, glue, suction, suture, or hook. The one or more joint tissues can include one or more of a fibrous capsule, subsynovium, synovial membrane, synovium, joint cavity, synovial fluid, articular cartilage, subchondral bone, or ligament. The one or more joints can include a synovial joint, cartilaginous joint, or fibrous joint.

In an aspect, the one or more applicators supported by the one or more substrates, e.g., one or more sheaths or patches, can be configured to respond to one or more sensors, wherein the one or more applicators are configured to inject the one or more medicaments to the one or more joint tissues of the mammalian subject. In an aspect, the applicator includes one or more high speed microjets, one or more microneedles, one or more microfine lances, one or more microfine cannulas, one or more microprojections, or one or more electrodes. The one or more applicators can include one or more high speed microjets, e.g., nanoliter-volume pulsed microjets. In an aspect, the applicator includes a fluid displacement actuator configured as one or more piezoelectric actuators, one or more springs, one or more solenoids, one or more magnets, one or more motors, or one or more compressed gas actuators.

In an aspect, the device can include medicament applicators including one or more high speed microjets. High speed microjets can deliver one or more medicaments by displacing the medicament solution through a micronozzle, e.g., 50-100 µm in final diameter. The high speed microjets can use one or more modes of fluid displacement, e.g., a piezoelectric actuator displacing a plunger, that provides a device or system having robustness and energy efficiency. The displacement of the plunger by the piezoelectric actuator can eject a microjet whose volume and velocity can be controlled by controlling the voltage and the rise time of the applied pulse to the piezoelectric actuator. At the end of the stroke, the plunger can be brought back to its original position by a compressed spring. The voltage applied to the piezoelectric crystal can be varied between 0 and 140 V to generate microjets with volumes up to 15 nanoliters. The frequency of pulses can be within a range of 0.1 to 10 Hz, e.g., 1 Hz. The medicament solution can be filled in a reservoir, which directly feeds the solution to the micronozzle of the microjet. The reservoir can be maintained at a slight overpressure, e.g., a small fraction of atmospheric pressure, to avoid backflow. In detailed aspects, the piezoelectric actuator, on application of a voltage pulse, can expand rapidly to push a plunger that ejects the fluid from the micronozzle as a high-speed microjet. The volume of the microjet is proportional to the amplitude of the voltage pulse, and the velocity of the microjet is proportional to the rise time. In further detailed aspects, a rise time of 10 µseconds would lead to a mean velocity of 127 meters/second for a 10-nanoliter microjet delivered from a 100-µm diameter micronozzle. For example, $v=Q/At$, where Q is the microjet volume, A is the cross-sectional area of the micronozzle, and t is the rise time. By controlling the amplitude and rise time of the pulse, velocity as well as volume of the microjet can be adjusted. Dispensed volume from the nozzle is replaced by liquid from the reservoir, which is maintained under slight positive pressure to avoid backflow. Under typical operating conditions, microjets can be ejected from the micronozzle at exit velocities exceeding 100 meters/second and volumes of 10 to 15 nanoliters. The microjets can be cylindrical in shape and each jet pulse could be clearly distinguished. To deliver volumes in excess of 10 to 15 nanoliters, the microjets can be designed to operate over a prolonged time period, and the total amount of liquid ejected will be proportional to the application time. In an aspect, a pulsation frequency of 1 Hz (1 microjet per second) can be used. This frequency can be increased if higher delivery rates are desired. See, e.g., Arora et al., *Proc. Natl. Acad. Sci. USA,* 104: 4255-4260, 2007, which is incorporated herein by reference. Other modes of fluid displacement from the high speed microjet include, but are not limited to, dielectric breakdown, electromagnetic displacement, springs, solenoids, motors, or compressed gas actuators.

In an aspect, the device includes medicament applicators including one or more microneedles that can be produced by microfabrication technology. Microneedles can be used to deliver the one or more medicaments through the stratum corneum barrier of the mammalian subject. The microneedles pierce into the skin to permit drug delivery, and are short and thin to avoid causing pain. The stratum corneum at the skin surface of the mammalian subject provides a barrier to drug transport into the body of the mammalian subject. A microneedle can be configured to cross the stratum corneum and deliver drugs into the permeable regions of skin without stimulating nerves found deeper in the tissue. Microneedles can be configured to pierce human skin and to increase, by two or more orders of magnitude and over time, skin permeability to small molecules and proteins. See, e.g., Kaushik et al., *Anesth. Analg.,* 92: 502-504, 2001; Henry S, et al., *J Pharm Sci.,* 87: 922-925, 1998; McAllister D, et al., *Proc Int Symp Control Rel Bioact Mater.,* 26: 192-193, 1999, each of which is incorporated herein by reference. In an aspect, the device including medicament applicators can be microfabricated as one or more microfine lances, one or more microfine cannulas, or one or more microprojections.

In an aspect, devices including solid microneedles can be used in combination with transdermal patch technology. Integrated into a patch, microneedles can provide a minimally invasive method to increase skin permeability for diffusion-based transport that could make transdermal delivery of many drugs possible, including that of large molecules such as proteins. Hollow microneedles, either as individual needles or as multineedle arrays, can be used for convection-based delivery. This microinfusion approach can increase rates of delivery beyond those of passive patches, and permit rates to be modulated in real time by a microprocessor-controlled pump, which can include a user interface for input by patients or by healthcare providers, or by a companion animal owner, animal caretaker or a livestock owner. See, e.g., McAllister et al., *Proc. Natl. Acad. Sci. USA,* 100: 13755-13760, 2003, which is incorporated herein by reference.

In an aspect, the device includes medicament applicators including one or more electrodes on microprojections configured to apply electrical energy to skin of the mammalian subject. The electrodes on microprojections provide ablation of stratum corneum in an area beneath the electrodes thereby generating a plurality of hydrophilic microchannels in the skin of the mammalian subject. The one or more medicaments can be delivered through the plurality of hydrophilic microchannels in the skin of the mammalian subject. See, e.g., U.S. Pat. No. 7,395,111; or U.S. 2005/0226922, each of which is incorporated herein by reference.

Piezoelectric actuators can be configured to displace plungers in the high speed microjets. The piezoelectric actuators can include capacitive transducers that expand when voltage is applied to them. The displacements of piezoelectric actuators are typically small (e.g., typically less than 10 µm), while the forces they generate can be quite large, from approximately 1 N to approximately 1000 N. Typically, the expansion of a piezoelectric actuator is limited by size, but large displacements which result in larger velocities can be desirable. One way to amplify the motion of a piezoelectric actuator is to use flexural hinges. Expansion of the piezoelectric actuator in the horizontal direction (x-x) can lead to a push or pull of hinges in the vertical direction (y-y). See, e.g., U.S. 2008/0091139, which is incorporated herein by reference.

In an aspect, the device includes the applicator configured as a compressed gas actuator to pressurize the chamber for delivery of the one or more medicaments through one or more high speed microjets. A compressed gas actuator is necessary to pressurize the central aperture of the one or more high speed microjets. The compressed gas actuator can take the form of a gas canister linked to a button cylinder, with operation of the button cylinder releasing a fixed amount of gas, for example 5 ml, enabling the gas source to be used to deliver sequentially a plurality of discrete payloads of one or more medicaments without needing to be recharged. Alternatively, a closed gas cylinder containing a single dose of gas can be sufficient for a single medicament delivery from the one or more high speed microjets. The gas source can include, e.g., helium, with the gas cylinder containing helium gas at a pressure of between approximately 15 bar and approximately 35 bar, or around 30 bar. Helium, as a driver gas, can provide much higher gas velocity than air, nitrogen, or $CO_2$.

In an aspect, the device includes an applicator supported by one or more sheaths and configured to inject one or more medicaments to a tissue of the one or more joints of the mammalian subject. The one or more sheaths can be configured to contact a body contour at one or more joints of articulating bone of the mammalian subject. The one or more sheaths can be a sleeve-shaped article of clothing or a sleeve-shaped body covering for one or more joints of articulating bone. The one or more sheaths including the one or more medicament applicators is aligned to the one or more joints of the mammalian subject, e.g., hand, wrist, elbow, shoulder, neck, foot, ankle, knee, or hip. The sheath or brace is aligned to surface architecture of the one or more joints of the mammalian subject. The sheath or brace can be held in a fixed position surrounding the joint by a variety of attachment mechanisms, e.g., elastic, adhesive, or VELCRO® hook and loop fastener. The applicator can deliver concentrated therapeutic medicaments directly to tissues of the one or more joints including one or more of a fibrous capsule, subsynovium, synovial membrane, synovium, joint cavity, synovial fluid, articular cartilage, subchondral bone, or ligament of the joint of the mammalian subject.

In an aspect, the device including the one or more sheaths can also include a pressure-exerting device or tourniquet to apply a constricting force and/or pressure on the applicator, e.g., microneedles, to ensure penetration of the stratum corneum of the mammalian subject. The device including the one or more sheaths can further apply pressure to the microneedles to ensure penetration of the microneedles directly into the one or more joint tissues including one or more of a fibrous capsule, subsynovium, synovial membrane, synovium, joint cavity, synovial fluid, articular cartilage, subchondral bone, and/or ligaments. See, e.g., U.S. 2009/0155341, which is incorporated herein by reference.

Delivery of the one or more medicaments to the one or more joints via the applicator can include a controller including a manually-activated switch. The manually activated switch can provide electric current to the applicator. This can be done "as needed" for pain and stiffness as determined by the mammalian subject, by a health care provider, or by a companion animal owner, animal caretaker or a livestock owner. The dose of one or more medicaments delivered can be determined by the concentration of the one or more medicaments in the reservoir and the duration of the electric current from the activated switch. A sensor including micro-circuitry can monitor the total dose of the one or more medicaments delivered within 24 hours and control drug delivery to prevent exceeding the maximum recommended dose to the mammalian subject. The device can include a controller in communication with the one or more sheaths via a sensor including micro-circuitry. The sensor including micro-circuitry can include a timer that allows the mammalian subject or a healthcare worker to program a dose and schedule for delivery of the one or more medicaments. The dosing schedule can span hours, days, weeks or months and the micro-circuitry can record and store total dosage and/or dosage within a fixed time period of hours, days, weeks or months. The device can transmit information through the sensor and the controller, including, but not limited to, drug dosage, schedule, and drug consumption to a computer network system that can be accessible by the mammalian subject, the subject's family, healthcare providers, insurance companies, regulatory authorities or public health officials.

In an aspect, the device including one or more sheaths configured to contact a body contour at one or more joints of articulating bone of a mammalian subject; and including a medicament applicator supported by the one or more sheaths can further include a sensor configured to detect a physiological condition of the mammalian subject. The sensor can be configured to detect one or more of movement of the contacted body contour, tissue swelling, tissue pressure, tissue color, tissue temperature, environmental temperature, electrical property of tissue, optical property of tissue, perspiration, or presence of an analyte. Temperature can refer to one or more of body temperature, tissue temperature, or environmental temperature. In detailed aspects, the device including the one or more sheaths can contain sensors to monitor the ambulatory movements of the patient and to actuate the applicator. The sensor can be, for example, an accelerometer, a bonded piezoelectric crystal, a mercury switch, or a gyro that generates a signal as a function of patient activity, e.g., body motion, footfalls or other impact events. One or more processors can determine an activity level based on a signal generated by one of these types of sensors. The one or more processors can be configured to sample the signal and determine a number of activity counts during the sample period. The processor can then store the determined number of activity counts in memory of a computing device as an activity level. The sensors can transmit information via the processor to a computer terminal for analysis or to the patient, healthcare workers, or caregivers. See, e.g., U.S. 2007/0250134 or U.S. 2007/0255118, each of which is incorporated herein by reference. In detailed aspects, the device including the sensor can include a wearable, hip-mounted movement monitor including a triaxial accelerometer that reports data to a microcontroller with micro-circuitry and software to monitor and record ambulatory movement of the mammalian subject. The triaxial accelerometer can include two orthogonally mounted dual axis accelerometers, e.g., MXR7210GL, available from MEMSIC, Inc., North Andover, Mass. The microcontroller can sample output signals from the accelerometers, and the data can be analyzed using a classification algorithm embedded in flash memory of the microcontroller, e.g., microcontroller MSP430F149, available from Texas Instruments, Dallas, Tex. See, e.g., Karantonis, et al., *IEEE Trans. Info. Tech. Biomed.* 10: 156-167, 2006, which is incorporated herein by reference. The movement sensor can distinguish a number of ambulatory states. For example the movement sensor can distinguish between periods of activity and rest, recognize postural orientation, detect walking, or provide an estimate of metabolic energy expenditure. The movement sensor and connected microcontroller can also include programming having predetermined parameters of posture, movement and metabolic energy expenditure. Such parameters can represent thresholds for the microcontroller to signal the actuators, e.g., solenoids, of the applicator. The microcontroller can instruct the actuators to deliver one or more medicaments to the one or more joint tissues of the mammalian subject. Parameters of posture, movement and energy expenditure can also be derived from historical data obtained with the movement sensor from the current patient or from previous patients. The movement sensor and microcontroller can transmit data on movement, posture, and energy expenditure to a computing device to analyze the data or to the patient, healthcare workers, and/or caregivers. The movement sensor and microcontroller can further transmit data on the dosing and scheduling of medicament delivery for the patient. The sheath device including a medicament applicator and motion sensors can further include a power source and micro-circuitry to control the dose and schedule of the one or more medicaments delivered to the one or more joint tissues of the mammalian subject. A power source including a lithium battery can provide electric current to drive solenoid actuator valves and a minipump that are connected to a therapeutic medicament reservoir and arrays of medicament applicators. In an aspect, the power source can include a motion-activated generator, e.g., piezoelectric actuator, hydraulic power, mechanical power, or spring-activated power, wherein the power source is powered by motion of the body of the mammalian subject. In further aspects, the battery can include, but is not limited to, a thin-film electrochemical cell, a lithium ion battery, a zinc-air battery, a lithium manganese oxide battery, a zinc manganese oxide battery, a lithium sulfuryl chloride battery, a lithium polymer battery, a lithium vanadium oxide battery, and a nickel metal hydride battery. See e.g., U.S. Pat. No. 5,338,625, which is incorporated herein by reference.

In an aspect, the device including one or more sheaths configured to contact a body contour at one or more joints of articulating bone of a mammalian subject, further including one or more sensors, can generate a signal as a function of patient activity and patient posture. The device can further include a controller configured to respond to the sensor and to activate the applicator supported by the one or more sheaths. For example, the sensors can include one or more of accelerometers, gyros, or magnetometers that can generate signals that indicate both the activity and the posture of a patient.

In an aspect, in order to identify posture, sensors such as accelerometers can be oriented substantially orthogonally with respect to each other. In addition to being oriented orthogonally with respect to each other, each of the sensors used to detect the posture of a patient can be substantially aligned with an axis of the body of a patient. When accelerometers, for example, are aligned in this manner, the magnitude and polarity of DC components of the signals generated by the accelerometers indicate the orientation of the patient relative to the Earth's gravity, e.g., the posture of a patient. See e.g., U.S. Pat. No. 5,593,431; or U.S. 2007/0250134, each of which is incorporated herein by reference.

Other sensors that can generate a signal to activate the device include sensors that include electrodes to generate a signal as a function of electrical activity within muscles of a patient, e.g., an electromyogram (EMG) signal, to indicate posture or activity of the patient. In an aspect, sensors can include bonded piezoelectric crystal that generates a signal as a function of contraction of muscles. Electrodes or bonded piezoelectric crystals can be implanted in the legs, buttocks, chest, abdomen, or back of a patient, and coupled to the device wirelessly or via one or more leads. Alternatively, electrodes can be integrated in a housing of the device or piezoelectric crystals can be bonded to the housing when the sensor is implanted in the buttocks, chest, abdomen, or back of a patient. The signals generated by such sensors when implanted in these locations can vary based on the posture of a patient, e.g., can vary based on whether the patient is standing, sitting, or lying down.

In a further aspect, the posture of a patient can affect the thoracic impedance of the patient. Sensors can include an electrode pair, including one electrode integrated within the housing of the device and one electrode in contact with an area of the patient's thorax, wherein the sensors can generate a signal as a function of the thoracic impedance of the patient. The controller in communication with the sensor can include a processor to detect the posture or postural changes of the patient based on the signal. The electrodes of the pair can be located on opposite sides of the patient's thorax. For example, the device can include one electrode pair located proximate to the spine of a patient for delivery of the anti-inflammatory medicament. In addition, the device with one electrode integrated in its housing and one electrode in the area of the patient's thorax can be implanted in the abdomen or chest of patient. In a further aspect, the device can include electrodes implanted to detect thoracic impedance in addition to leads implanted within the brain of the patient. The posture or postural changes can affect activation of the device for the delivery of the anti-inflammatory medicament to the patient for the treatment of an inflammatory disorder of the joints of the patient.

Additionally, changes in the posture of a patient can cause pressure changes within the cerebrospinal fluid (CSF) of the patient. Consequently, sensors can include pressure sensors coupled to one or more intrathecal or intracerebroventricular catheters, or pressure sensors coupled to the device wirelessly or via leads. CSF pressure changes associated with postural changes can be particularly evident within the brain of the patient, e.g., can be particularly apparent in an intracranial pressure (ICP) waveform.

In an aspect, the processor can monitor a signal that indicates a physiological parameter of a patient, which in turn varies as a function of patient activity. For example, the processor can monitor a signal that indicates movement of the contacted body contour, tissue swelling, tissue pressure, tissue color, tissue temperature, environmental temperature, electrical property of tissue, optical property of tissue, perspiration, or presence of an analyte in the patient. In an aspect, the processor can periodically determine a measured value of one or more sensor configured to detect movement of the contacted body contour, tissue swelling tissue pressure, tissue color, tissue temperature, environmental temperature, electrical property of tissue, optical property of tissue, perspiration, or presence of an analyte in the patient based on the signal. Temperature can refer to one or more of body temperature, tissue temperature, or environmental temperature. The determined values of these parameters can be, for example, mean or median values. See, e.g., U.S. Pat. No. 5,593,431; U.S. 2007/0250134, each of which are incorporated herein by reference.

In an aspect, the device can include one or more sheaths and a medicament applicator supported by the one or more sheaths configured to inject one or more medicaments to one or more joint tissues, wherein the device includes a pharmaceutical composition including the one or more medicaments in a thixotropic medium. The pharmaceutical composition including the one or more medicaments in a thixotropic medium promotes delivery of high concentrations of the one or more medicaments to the one or more joint tissues. Thixotropic media, e.g., α-cyclodextrin and carteolol hydrochloride, are useful for pharmaceutical applications because thixotropic pharmaceutical compositions display reduced viscosity when subjected to shear stress such as high velocity flow through the applicator, e.g., a microjet applicator. See, e.g., U.S. Pat. No. 6,143,329 entitled "Aqueous-based pharmaceutical composition" issued to Kim on Nov. 7, 2000, which is incorporated herein by reference. For example, parenteral injection of a thixotropic suspension of a pharmaceutical mixed with a small amount of polysorbate 80 (Mallincrodt Baker, Inc., Phillipsburg, N.J.) in water is decomposed to a liquid during passage through a medicament applicator, but regains a hydrogel structure and forms cohesive depots in the body. See Lee et al., *J. Contr. Rel.* 136: 88-98, 2009, which is incorporated herein by reference. Semisolid formulations comprised of solid lipid nanoparticles loaded with pharmaceuticals and CARBOPOL® 934 poly(acrylic acid) microgel have thixotropic properties. See Lee et al., Ibid. A particulate thixotropic medium combined with an anti-inflammatory medicament and co-delivered at high velocity to one or more joint tissues of the mammalian subject can achieve increased penetration of one or more of epidermal tissue, fibrous capsule, subsynovial tissue or synovial membrane. Moreover, the properties of the pharmaceutical formulation including thixotropic medium can lead to formation and deposition of the anti-inflammatory medicament as a viscous liquid or hydrogel solution in the one or more joint tissues and in the joint synovial cavity of the mammalian subject.

A system is described that includes an apparatus including a sensor configured to detect one or more physiological conditions of one or more joints of articulating bone of a mammalian subject, and a controller configured to communicate with the sensor. The controller can be configured to activate the device including one or more sheaths configured to contact one or more body contours in proximity to one or more joints of articulating bone of the mammalian subject. The device can further include one or more microjet applicators supported by the one or more sheaths and configured to inject one or more medicaments to one or more joint tissues of the mammalian subject.

A method is described that includes injecting one or more medicaments to one or more joint tissues of a mammalian subject, wherein the injecting of the one or more medicaments is by a device that includes one or more sheaths configured to contact one or more body contours in proximity to one or more joints of articulating bone of the mammalian subject, and one or more microjet applicators supported by the one or more sheaths and configured to inject one or more medicaments to one or more joint tissues of the mammalian subject.

A method is described that includes producing a device configured to inject one or more medicaments to one or more joint tissues of a mammalian subject, wherein the device includes one or more sheaths configured to contact one or more body contours in proximity to one or more joints of articulating bone of the mammalian subject, and one or more microjet applicators supported by the one or more sheaths and configured to inject one or more medicaments to one or more joint tissues of the mammalian subject. The applicator can include, but is not limited to, one or more high speed microjets, one or more microneedles, one or more microfine lances, one or more microfine cannulas, one or more microprojections, or one or more electrodes. The one or more sheaths can be configured to contact the one or more body contours in proximity to the one or more joints of the mammalian subject. The method can further include providing a sensor configured to detect a physiological condition of the mammalian subject. The sensor can be configured to detect movement of the contacted body contour, tissue swelling, tissue pressure, tissue color, tissue temperature, environmental temperature, electrical property of tissue, optical property of tissue, perspiration, or presence of an analyte. Temperature can refer to one or more of body temperature, tissue temperature, or environmental temperature. The method can further include providing a controller configured to respond to the sensor, the controller configured to control release of the one or more medicaments from the applicator. The controller can be configured to control a timed release of the one or more medicaments. The sensor can be configured to monitor joint movement, body movement, or gait of the mammalian subject. The sensor can be configured to monitor posture of the mammalian subject The applicator can be configured to respond to the sensor detecting movement of the contacted body contours, wherein the one or more applicators are configured to inject the one or more medicaments into the one or more joint tissues of the mammalian subject.

A device is described that includes an enclosure including one or more sensors, a controller, and one or more applicators configured to surround one or more joints of articulating bone of a mammalian subject. The one or more sensors are distributed within the enclosure and are configured to detect one or more physiological conditions of one or more joints as they are placed within the enclosure by the mammalian subject. The controller can be configured to communicate with the sensor, wherein the controller is configured to activate the one or more applicators supported by one or more substrates configured to contact one or more body contours in proximity to the one or more joints of the mammalian subject. The controller in combination with the sensor can be configured to position the one or more applicators to locate the applicators near the one or more joints. When the one or more applicators are located near the one or more joints, the one or more applicators are configured to inject one or more medicaments to the one or more joint tissues of the mammalian subject. In an aspect, the sensor can be configured to detect the one or more physiological conditions of the one or more joints by ultrasonic imaging of the one or more joints. A liquid can be configured between an ultrasonic transducer and the one or more joints for the ultrasonic imaging of the one or more joints of the mammalian subject. In a further aspect, the one or more sensors can be configured to detect the one or more physiological conditions of the one or more joints by X-ray imaging of the one or more joints. In a further aspect, the one or more joints can include, for example, one or more of hand joints, wrist joints, elbow joints, or shoulder joints; or one or more of foot joints, ankle joints, knee joints, or hip joints.

In an aspect, the one or more medicaments can include, but is not limited to, steroids, corticosteroids, analgesics, anti-inflammatories, or NSAIDs. The device can deliver the one or more medicaments to the one or more joints of the mammalian subject compared to systemic delivery of the one or more medicaments. NSAIDs can include, but are not limited to, acemetacin, amtolmetin, azapropazone, benorilate, benoxaprofen, benzydamine hydrochloride, bromfenal, bufexamac, butibufen, carprofen, celecoxib, choline salicylate, dipyone, droxicam, etodolac, etofenamate, etoricoxib, felbinac, fentiazac, floctafenine, indoprofen, isoxicam, lomoxicam, loxoprofen, licofelone, fepradinol, magnesium salicylate, meclofenamic acid, meloxicam, morniflumate, niflumic acid, nimesulide, oxaprozen, piketoprofen, priazolac, pirprofen, propyphenazone, proquazone, rofecoxib, salalate, sodium salicylate, sodium thiosalicylate, suprofen, tenidap, tiaprofenic acid, trolamine salicylate, or zomepirac. The NSAID can further include, but is not limited to, aclofenac, aloxiprin, naproxen, aproxen, aspirin, diclofenac sodium, diflunisal, fenoprofen, indomethacin, mefenamic acid, piroxicam, phenylbutazone, salicylamide, salicylic acid, sulindac, desoxysulindac, tenoxicam, tramadol, ketoralac, clonixin, fenbufen, benzydamine hydrochloride, meclofenamic acid, flufenamic acid, or tolmetin. See, e.g., U.S. Pat. No. 7,387,789, U.S. Pat. No. 6,818,226, or U.S. Pat. No. 5,374,661, each of which is incorporated herein by reference. The NSAID can further include, but is not limited to, choline magnesium trisalicylate (TRILISATE®), diflunisal)(DOLOBID®), fenoprofen (NALFON®), flurbiprofen (ANSAID®), ketoprofen (ORUDIS®, ACTRON®, or ORUVAIL®), nabumetone (RELAFEN®), or salsalate (SALFLEX®, DISALCID®, or AMIGESIC®). Anti-inflammatory agents, include, but are not limited to, betamethasone 21-phosphate disodium salt, triamcinolone acetonide 21disodium phosphate, hydrocortamate hydrochloride, hydrocortisone 21-phosphate disodium salt, methylprednisolone 21-phosphate disodium salt, methylprednisolone 21-succinaate sodium salt, paramethasone disodium phosphate and prednisolone 21-succinate sodium salt, and anticoagulants, such as citric acid, citrate salts (e.g., sodium citrate), dextrin sulfate sodium, and EDTA. See, e.g., U.S. 2006/0036209, which is incorporated herein by reference.

One or more therapeutic medicaments, alone or in combination with other drugs or agents, formulated for delivery to a tissue of one or more joints of a mammalian subject, can be prepared as pharmaceutical compositions that contain one or more added materials such as carriers, vehicles, and/or excipients. "Carriers," "vehicles" and "excipients" generally refer to substantially inert materials that are nontoxic and do not interact with other components of the composition in a deleterious manner. Exemplary carriers, vehicles, or excipients can be found, e.g., in the U.S. Food and Drug Administration inactive ingredients database Examples of suitable carriers include, but are not limited to, water, silicone, gelatin, or waxes. Examples of normally employed "excipients," include, but are not limited to, pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, or high molecular weight polyethylene glycols (PEG), or combinations thereof. In addition, it may be desirable to include a charged lipid and/or detergent in the pharmaceutical compositions. Such materials can be used as stabilizers or antioxidants, or used to reduce the possibility of local irritation at the site of administration. Suitable charged lipids include, but are not limited to, phosphatidylcholines (lecithin). Detergents will typically be a nonionic, anionic, cationic or amphoteric surfactant. Examples of suitable surfactants include, for example, TERGITOL® and TRITON® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS).

Figure 1B:
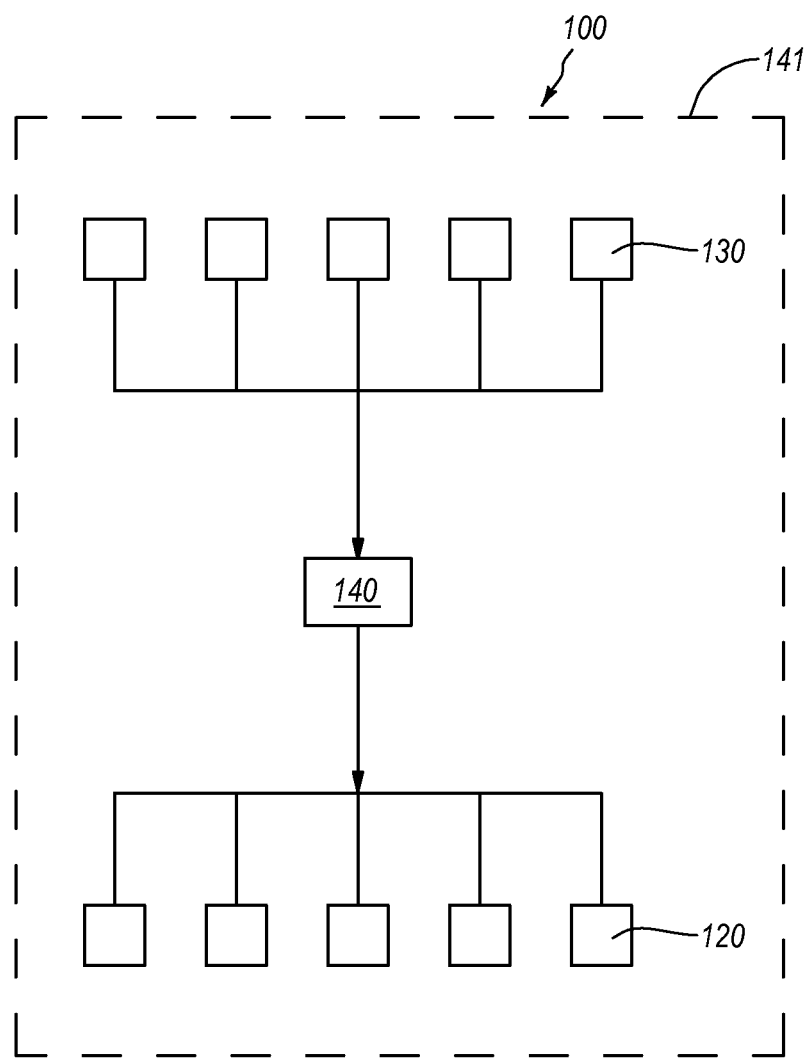
Figure 1C:
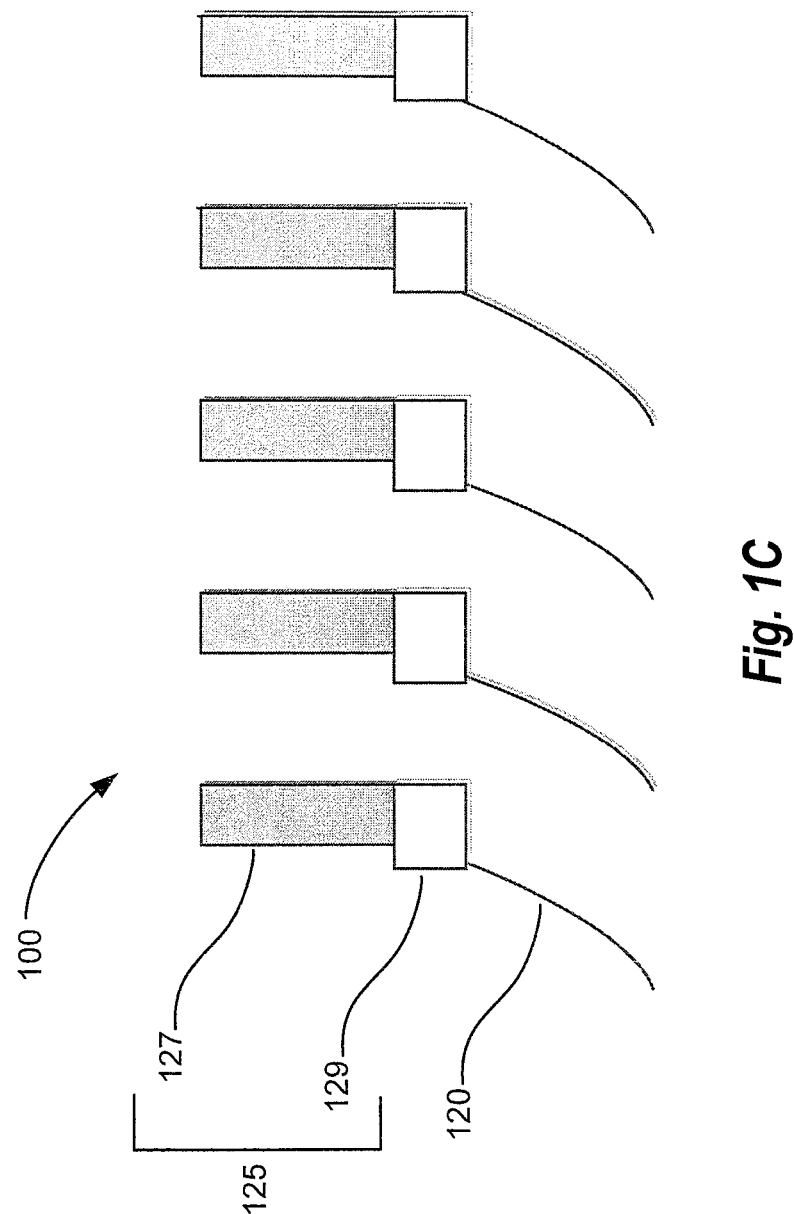
Figure 2A:
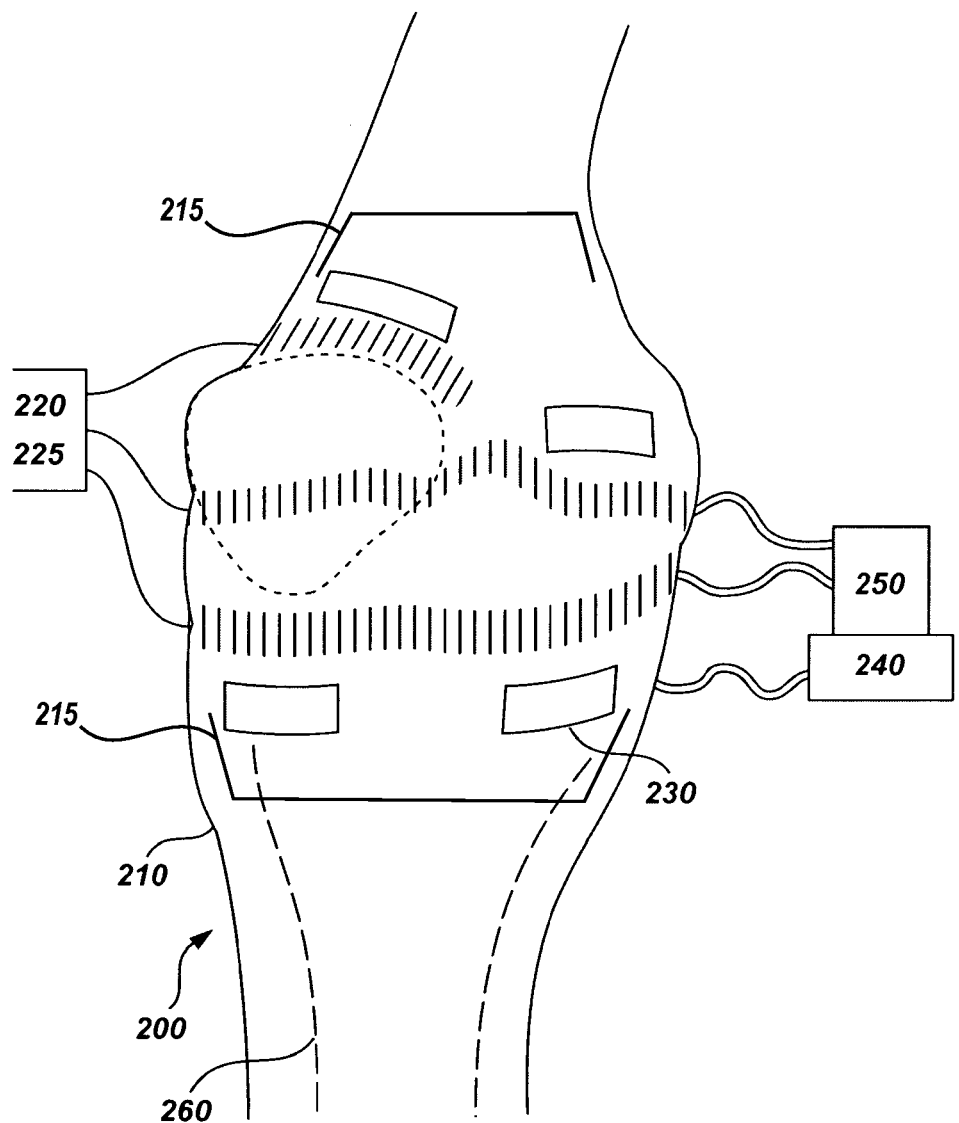
FIGS. 2A and 2B depict a diagrammatic view of an aspect of a device.
Figure 2B:
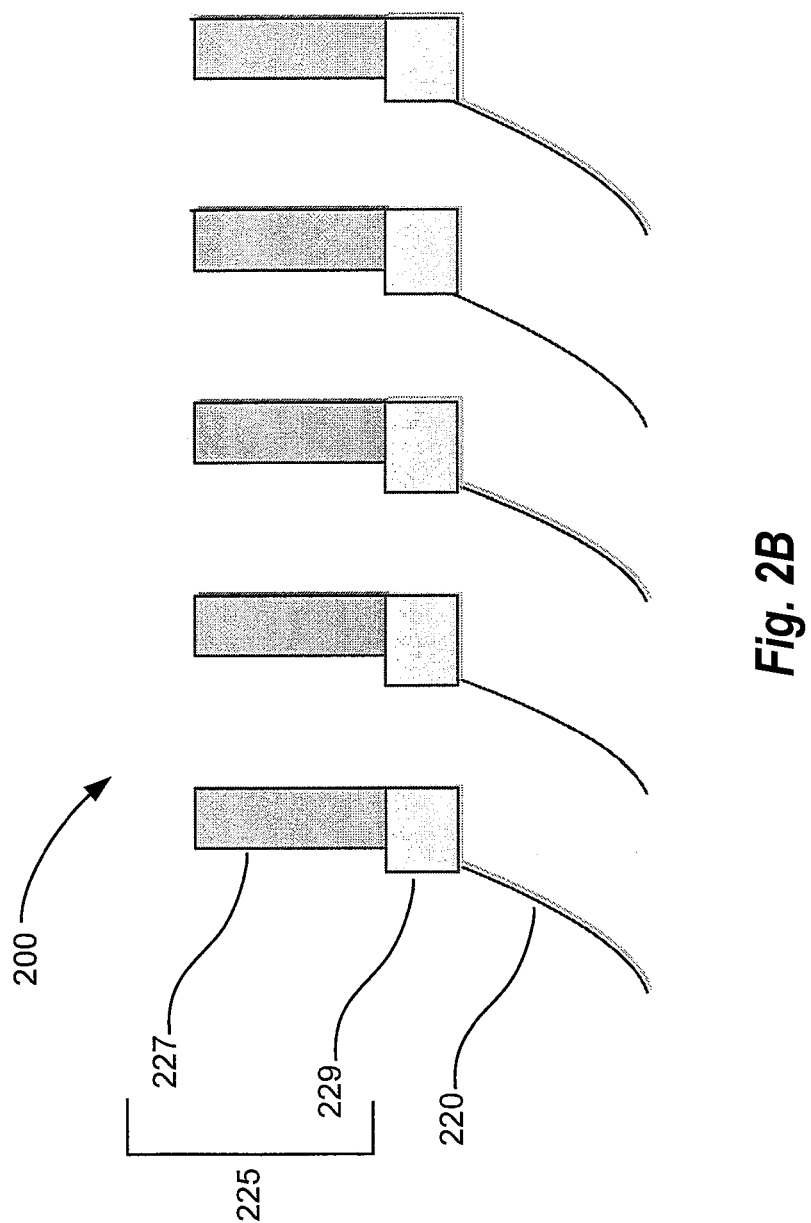

With reference to the figures, and with reference now to FIGS. 1 and 2 depicted is an aspect of a device or method that can serve as an illustrative environment of and/or for subject matter technologies, for example, a device including one or more sheaths configured to contact a body contour at one or more joints of articulating bone of a mammalian subject; and an applicator supported by the one or more sheaths and configured to inject one or more medicaments to a tissue of the one or more joints of the mammalian subject.

FIG. 1A depicts a diagrammatic view of an aspect of a device 100. The device 100 includes one or more sheaths 110 configured to contact a hand 160 at one or more joints of articulating bone in the hand of a mammalian subject, and an applicator 120, e.g., one or more of high speed microjets, microneedles, microfine lances, microfine cannulas, microprojections, or electrodes, supported by the one or more sheaths 110 and configured to inject one or more medicaments to a tissue of the one or more joints of the mammalian subject. The device can further include a sensor 130 configured to detect a physiological condition of the mammalian subject such as, for example, a sensor to detect movement of the contacted body contour, a sensor to detect tissue swelling, tissue pressure, or tissue color, a sensor to detect tissue temperature, environmental temperature, a sensor to detect electrical property of tissue, optical property of tissue, or perspiration, or a sensor to detect presence of an analyte. The device 100 can further include a controller 140 in communication with the sensor 130, the applicator 120, and the fluid displacement actuator 125. As shown in FIG. 1B, in an embodiment, a desktop device 141 can include the controller 140, sensors 130, and applicators 120, and the controller 140 in combination with one or more of the sensors 130 can be configured to position the one or more applicators 120 to locate the one or more applicators 120 near the one or more joints. The controller is configured to activate the fluid displacement actuator 125 and the applicator 120 utilizing a component 150 for transient mechanical/electrical acceleration of the one or more medicaments from the applicator 120.

FIG. 1C depicts a diagrammatic view of an aspect of one or more fluid displacement actuators 125 and applicators 120 of a device 100. The fluid displacement actuator 125 can include a piezoelectric actuator 127 displacing a plunger 129. The applicator 120 can include, for example, a micronozzle of a high speed microjet or a microneedle. The piezoelectric actuator 127, on application of a voltage pulse, can expand rapidly to push the plunger 129 that ejects the fluid from the applicator 120, e.g., through a micronozzle as a high-speed microjet, or through a microneedle.

FIG. 2 depicts a diagrammatic view of an aspect of a device 200. The device 200 includes one or more sheaths 210 configured to contact a leg and knee 260 at one or more joints of articulating bone in the hand of a mammalian subject, and an applicator 220, e.g., one or more of high speed microjets, microneedles, microfine lances, microfine cannulas, microprojections, or electrodes, supported by the one or more sheaths 210 and configured to inject one or more medicaments to a tissue of the one or more joints of the mammalian subject. The device can further include a sensor 230 configured to detect a physiological condition of the mammalian subject. The device can further include a controller 240 in communication with the sensor 230 and the fluid displacement actuator 225. The controller is configured to activate the fluid displacement actuator 225 and the applicator 220 utilizing a component 250 for transient mechanical/electrical acceleration of the one or more medicaments from the applicator 220.

Figure 3:
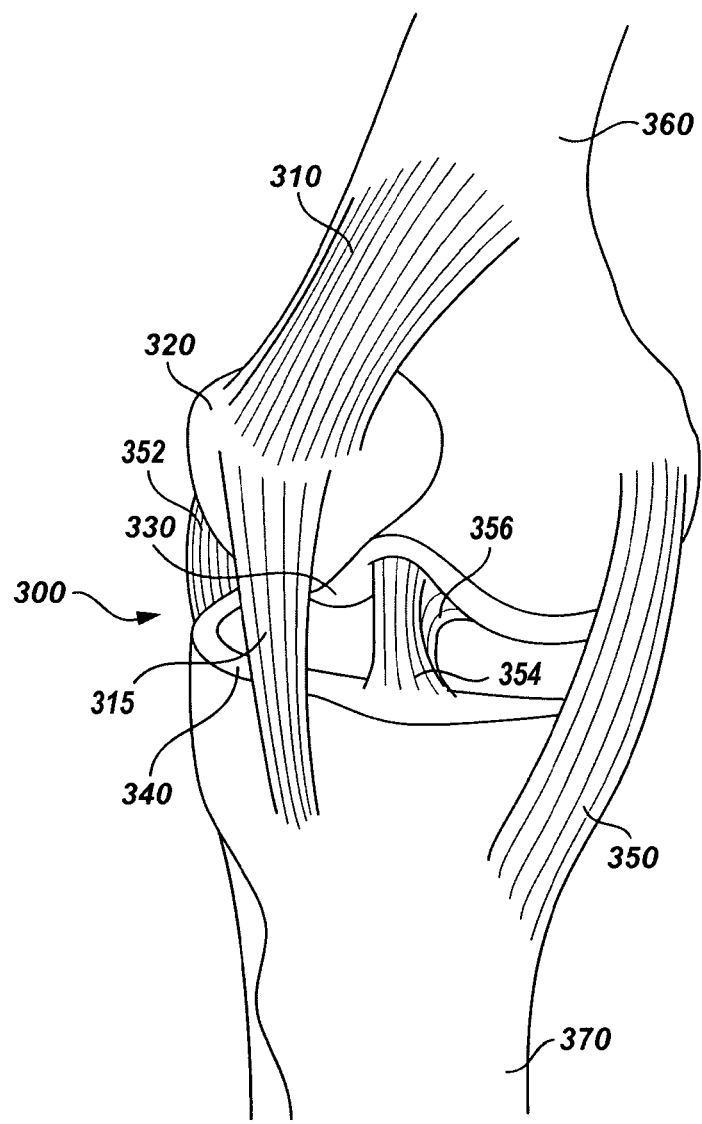
FIG. 3 depicts a diagrammatic view of an aspect of a knee joint.

FIG. 3 illustrates an exemplary aspect of a knee joint 300. The knee joint 300 is the junction of three bones: the femur 360, the tibia 370, and the patella 320. The patella is 2 to 3 inches wide and 3 to 4 inches long. It protects the knee and gives leverage to muscles. The ends of the three bones in the knee joint 300 are covered with articular cartilage 330 that helps absorb shock and allows the knee joint 300 to move smoothly. Separating the bones of the knee are two crescent-shaped discs of connective tissue called menisci 340. The menisci 340 are positioned between the tibia 370 and femur 360 on the outer and inner sides of each knee. The two menisci in each knee act as shock absorbers, cushioning the lower part of the leg from the weight of the rest of the body as well as enhancing stability. The quadriceps tendon 310 connects the quadriceps muscle to the patella and provides the power to straighten the knee. The patellar tendon 315 connects the tibia to the patella. Four ligaments connect the femur and tibia and give the knee joint 300 strength and stability. The medial collateral ligament (MCL) 350, which runs along the inside of the knee joint 300, provides stability to the medial part of the knee. The lateral collateral ligament (LCL) 352, which runs along the outside of the knee joint 300, provides stability to the lateral part of the knee. The anterior cruciate ligament (ACL) 354, in the center of the knee, limits rotation and the forward movement of the tibia. The posterior cruciate ligament (PCL) 356, also in the center of the knee, limits backward movement of the tibia. The knee capsule is a protective, fiber-like structure that wraps around the knee joint 300. Inside the capsule, the knee joint 300 is lined with a thin, soft tissue called synovium.

Figure 4:
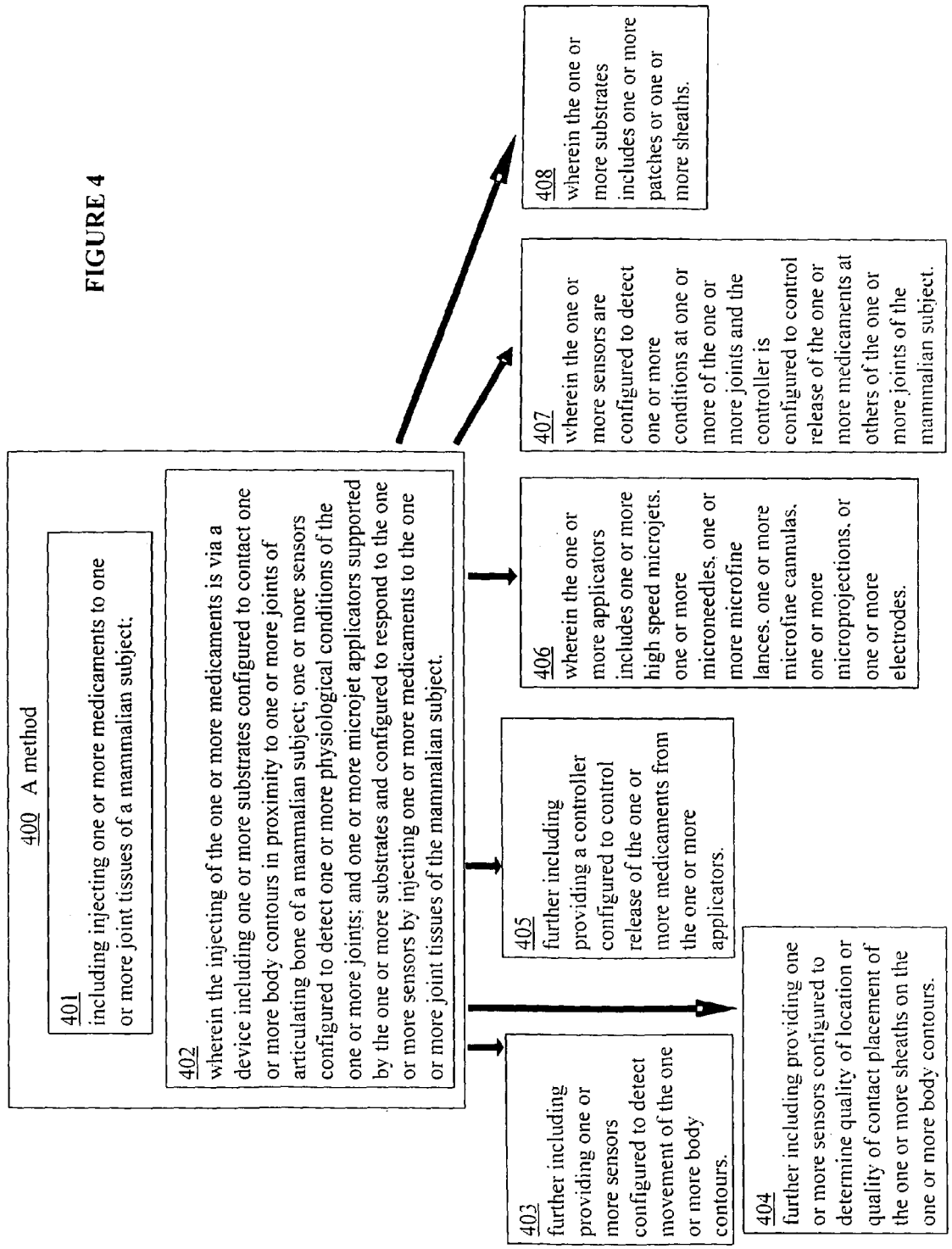
FIG. 4 illustrates an exemplary method that includes injecting one or more medicaments to one or more joint tissues of a mammalian subject via a device.

FIG. 4 illustrates an exemplary method including injecting one or more medicaments to one or more joint tissues of a mammalian subject. The method 400 comprises injecting 401 one or more medicaments to one or more joint tissues of a mammalian subject, wherein the injecting of the one or more medicaments is via a device 402 including one or more substrates configured to contact one or more body contours in proximity to one or more joints of articulating bone of a mammalian subject; one or more sensors configured to detect one or more physiological conditions of the one or more joints; and one or more microjet applicators supported by the one or more substrates and configured to respond to the one or more sensors by injecting one or more medicaments to the one or more joint tissues of the mammalian subject. The method can further include providing one or more sensors 403 configured to detect movement of the one or more body contour. The method can further include providing one or more sensors 404 configured to determine quality of location or quality of contact placement of the one or more sheaths on the one or more body contours. The method can further include providing a controller 405 configured to control release of the one or more medicaments from the one or more applicators. In an aspect, the one or more applicators 406 includes one or more high speed microjets, one or more microneedles, one or more microfine lances, one or more microfine cannulas, one or more microprojections, or one or more electrodes. In a further aspect, the one or more sensors 407 are configured to detect one or more conditions at one or more of the one or more joints and the controller is configured to control release of the one or more medicaments at others of the one or more joints of the mammalian subject. In a further aspect, wherein the one or more substrates 408 includes one or more patches or one or more sheaths.

The methods and compositions are further described with reference to the following examples; however, it is to be understood that the methods and compositions are not limited to such examples.

EXAMPLES

Example 1

A Knee Brace Device with Embedded Microjets and Piezoelectric Actuators Configured to Deliver Naproxen (e.g., Naprosyn®) to an Arthritic Knee at High Local Concentrations in a Time Dependent Manner A device is provided to treat a patient with an arthritic knee. The device is a knee brace that is worn on the knee and delivers high local concentrations of an anti-inflammatory drug to the knee joint using microjets that are driven by piezoelectric actuators. The patient who has chronic pain and stiffness in a knee joint is clinically diagnosed to have moderate osteoarthritis as confirmed by radiography. To reduce pain and stiffness, a knee brace device is wrapped to contact the affected knee and positioned to substantially align multiple embedded microjets with one or more of the superior, inferior, lateral, medial, posterior or anterior aspects of the knee joint. The multiple embedded microjets are configured to provide transdermal delivery of highly concentrated therapeutic medicaments localized to the knee joint and may effectively deliver the therapeutic medicaments to tissues of the knee joint without risk of adverse reactions associated with oral systemic medicament. The device can deliver highly concentrated therapeutic medicaments to tissues of the knee joint including one or more of a fibrous capsule, subsynovium, synovial membrane, synovium, joint cavity, synovial fluid, articular cartilage, subchondral bone, or ligament. The knee brace device is held in place by VELCRO® strips and alignment of the microjets to the synovial joint is referenced to the knee cap and to an opening in the knee brace. Alternatively, the knee brace device may be an elastic sleeve with embedded microjets aligned to the knee joint by visual inspection when it is slipped over the knee. The microjets are connected to a reservoir containing naproxen (NAPROSYN®, available from Roche Laboratories, Nutley, N.J.) to provide anti-inflammatory medicament for repeated local delivery to the knee joint. Local delivery of concentrated naproxen solutions (e.g., approximately 25-200 mg/ml) may be achieved while avoiding potential adverse reactions. For example, a single microjet activated with a piezoelectric crystal may transdermally deliver approximately 28 mg of a drug in a day from a reservoir with a 20 mg/ml solution of drug. See, e.g., Arora et al., *Proc. Natl. Acad. Sci. USA*, 104: 4255-4260, 2007, which is incorporated herein by reference. Localized dosing of a concentrated naproxen suspension (e.g., NAPROSYN® suspension 25 mg/ml, available from Roche Laboratories, Nutley, N.J.) at the knee joint may be accomplished with a knee brace device containing multiple embedded microjets actuated by piezoelectric actuators that are controlled electronically using a lithium battery as a source of power. Piezoelectric crystal actuators expand when electronically activated to drive small liquid volumes (e.g., 10-15 nanoliters) through a microjet at high velocity (greater than 100 meter/sec). The high velocity (v>100 m/s) of microjets allows their entry into the skin, whereas the small jet diameters (50-100 μm) and extremely small volumes (2-15 nanoliters) limit the penetration depth (~200 μm) See, e.g., U.S. 2008/0091139 entitled "Methods, Devices and Kits for Microjet Drug Delivery" published Apr. 17, 2008; and Arora et al., Ibid. The rate of drug delivery may be modulated by varying the electronic signal frequency. For example, electronic signals to piezoelectronic crystals at 10 Hz actuate microjets ten times faster than 1 Hz signals and increase the rate of drug delivery by ten-fold. See, e.g., Arora et al., Ibid. In addition, the dosing of naproxen may also be controlled by variation of the drug concentration in the reservoir. Drug solutions or suspensions may be approximately 2 mg/ml, up to approximately 20 mg/ml, or up to approximately 200 mg/ml.

The knee brace device may be worn throughout the day and activated as needed by the patient via an electronic switch that controls the piezoelectric actuators driving multiple microjets. For example an electronic switch on the knee brace device may be turned on voluntarily by the patient "as needed" in response to pain and stiffness. Micro-circuitry, including a timer in the knee brace device may determine the duration of drug delivery (and therefore dose) following activation of the device. Alternatively, the knee brace device with micro-circuitry may be programmed to periodically deliver naproxen transdermally throughout the day and night on a predetermined dose and schedule as determined by the patient or the patient's physician with no need for manual activation.

Example 2

A Device Including a Sheath Bandage Containing Embedded Microneedles to Deliver Diclofenac Sodium (e.g., Voltaren® at High Local Concentration to Joint Tissue in a Time Dependent Manner to Treat a Patient with Osteoarthritis in a Wrist Joint A device is provided to treat a patient with osteoarthritis of the wrist. The device is a sheath bandage that is worn on the wrist and delivers high local concentrations of an anti-inflammatory drug to the wrist joint using microneedles that deliver drugs at high concentrations through the skin to wrist joint tissues and to the synovial cavity. The patient who has chronic pain and stiffness in a wrist joint is clinically diagnosed to have moderate osteoarthritis as confirmed by radiography. To reduce pain and stiffness a wrist sheath bandage device is applied to contact the affected wrist and positioned to align multiple embedded microneedles with the wrist joint. The multiple embedded microneedles are configured to provide transdermal delivery of highly concentrated therapeutic medicaments localized to the wrist joint and may effectively deliver the therapeutic medicaments to tissues of the wrist joint including one or more of a fibrous capsule, subsynovium, synovial membrane, synovium, joint cavity, synovial fluid, articular cartilage, subchondral bone, and/or ligaments without risk of adverse reactions associated with oral systemic medicaments.

The wrist sheath bandage device is held in place by adhesive strips and alignment of the microneedles to the wrist joint is referenced to palpable projections of the pelvic bone, specifically, the anterior superior iliac spine, and of the femur, specifically, the greater trochanter. The wrist sheath bandage device may alternatively be an elastic band with embedded microneedles aligned to the wrist joint by visual inspection. The wrist sheath bandage device may also have a tourniquet to apply a constricting force and/or pressure on the microneedles to insure penetration of the stratum corneum. A pressure-exerting element for applying pressure to an elastic body is described in Gavriely, et al., U.S. 2009/0155341 A1 entitled "Medical Device and A Method for Applying A Biochemically Active Material On One or More Body Parts" published Jun. 18, 2009 which is incorporated herein by reference. The wrist sheath bandage device may further apply pressure on the microneedles to insure penetration of the microneedles directly into the one or more joint tissues including one or more of a fibrous capsule, subsynovium, synovial membrane, synovium, joint cavity, synovial fluid, articular cartilage, subchondral bone, and/or ligaments. The microneedles are connected to a reservoir containing diclofenac (VOLTAREN®, available from Novartis Pharmaceuticals Corp., East Hanover, N.J.) to provide an anti-inflammatory and analgesic medicament for repeated local delivery to the wrist joint. Local delivery of concentrated diclofenac solutions, e.g., 200 mg/ml, may be achieved while maintaining low plasma concentrations and avoiding potential adverse reactions observed with oral administration. An oral dose of 75 mg diclofenac sodium results in a mean peak plasma concentration equal to 1.9 μg/ml, while topical diclofenac sodium (PENNSAID® available from Nuvo Research Inc., Mississauga, Ontario, Canada) reaches a mean peak plasma concentration of 11.8±4.2 ng/ml. See Ozguney, *Expert Opin. Pharmacother.*, 9: 1805-1816, 2008, which is incorporated herein by reference.

The wrist sheath bandage device contains a medicament applicator comprised of hollow microneedle arrays that are connected to a reservoir containing medicaments. Hollow microneedle arrays may be fabricated using microfabrication technology adapted from the microelectronics industry. For example silicon hollow microneedle arrays may be fabricated by etching holes through silicon wafers using deep reactive ion etching and then etching microneedles around the holes. See, e.g., McAllister et al., *Proc. Natl. Acad. Sci. USA*, 100: 13755-13760, 2003, which is incorporated herein by reference. Microneedle arrays (10×10) containing approximately 100 to approximately 400 microneedles in an area of 3 mm×3 mm are constructed with conical microneedles approximately 150 μm in length; with a base diameter of approximately 80 μm and a tip with approximately a 1 μm radius of curvature. Hollow microneedles with diameters between 35 μm and 300 μm and lengths between 150 μm and 1000 μm may be fabricated as shown by McAllister et al., Ibid. Alternatively hollow microneedles may be fabricated from metals, e.g., Ni or NiFe, or polymers, e.g., polyglycolic acid and poly lactic acid, by using micromolds or by electroplating polymer microneedles with nickel as shown by McAllister et al., Ibid. Hollow microneedle arrays may be connected via a manifold to a mini-pump, solenoid valve actuators and to a reservoir containing medicaments. Mini-pumps and solenoid valves are available from Parker-Hannifin, Precision Fluidics Division, Hollis, N.H. The applicator, comprised of hollow microneedle arrays, solenoid valve actuators, a minipump and a reservoir is embedded in the wrist sheath bandage device with the hollow microneedles facing the stratum corneum overlaying the wrist joint. Multiple medicament applicator units may be supported by the wrist sheath bandage device to align with different aspects of the wrist joint, e.g., anterior, posterior, lateral, medial, superior, inferior.

The wrist sheath bandage device with a medicament applicator has a power source and micro-circuitry to control the dose and schedule of diclofenac sodium delivered to the wrist joint. A lithium battery may provide electric current to drive solenoid actuator valves and a minipump which are connected to a medicament reservoir and microneedle arrays. The wrist sheath bandage device may apply pressure on the microneedles to insure penetration of the stratum corneum, epidermis, or dermis. The wrist sheath bandage device may further apply pressure on the microneedles to insure penetration of the microneedles directly into the one or more joint tissues including one or more of a fibrous capsule, subsynovium, synovial membrane, synovium, joint cavity, synovial fluid, articular cartilage, subchondral bone, and/or ligaments.

Delivery of diclofenac may be manually controlled by flipping a switch which provides electric current to the applicator. This may be done "as needed" for pain and stiffness. The dose of diclofenac sodium delivered may be determined by the concentration of diclofenac in the reservoir and the duration of the electric current. Micro-circuitry may monitor the total dose of diclofenac delivered within 24 hours and control drug delivery to prevent exceeding the maximum recommended dose. The wrist sheath bandage device may also have micro-circuitry including a timer that allows the patient, or a healthcare worker to program a dose and schedule of diclofenac sodium delivery. The dosing schedule may span hours, days, weeks or months and the micro-circuitry can record and store total dosage and/or dosage within a fixed time period of hours, days, weeks or months. The wrist sheath bandage device may transmit information including drug dosage, schedule, and drug consumption to a computer network system that includes the patient, the patient's family, healthcare providers, insurance companies, regulatory authorities and public health officials.

Example 3

A Sheath Device with Microneedle Arrays and Sensors to Monitor Movement and Deliver Naproxen (e.g., Naprosyn®) to the Hip Joint of A Patient with Osteoarthritis A device is provided to treat a patient with osteoarthritis of the hip. The device includes one or more sheaths that is worn on the hip and delivers high local concentrations of an anti-inflammatory drug to the hip joint using microneedles that deliver drugs at high concentrations through the skin to hip joint tissues and to the synovial cavity. The device also contains sensors to monitor the gait of the patient and to signal the applicator to deliver an anti-inflammatory, naproxen. The patient who has chronic pain and stiffness in a hip joint is clinically diagnosed to have moderate osteoarthritis as confirmed by radiography. To reduce pain and stiffness and to improve mobility a hip sheath device is applied to contact the affected hip and positioned to align multiple embedded microneedles with the hip joint as well as sensors to monitor the patient's gait. The multiple embedded microneedles are configured to provide transdermal delivery of highly concentrated therapeutic medicaments localized to the hip joint and may effectively deliver the therapeutic medicaments to tissues of the hip joint including one or more of a fibrous capsule, subsynovium, synovial membrane, synovium, joint cavity, synovial fluid, articular cartilage, subchondral bone, and/or ligaments. The device delivers the highly concentrated therapeutic medicaments localized to the hip joint without risk of adverse reactions associated with oral systemic medicaments.

The hip sheath device is slipped over the hip and alignment of the microneedles to the hip joint is referenced to palpable projections of the pelvic bone, specifically, the anterior superior iliac spine, and of the femur, specifically, the greater trochanter. The hip sheath device also has sensors to monitor the arthritic patient's gait. A sensor to monitor gait is described by Miesel et al., U.S. 2007/0250134 A1 entitled "Collecting Gait Information for Evaluation and Control of Therapy" published Oct. 25, 2007 which is incorporated herein by reference. The hip sheath device may also have a tourniquet to apply a constricting force and/or pressure on the microneedles to insure penetration of the stratum corneum. The hip sheath device may further apply pressure on the microneedles to insure penetration of the microneedles directly into the one or more joint tissues including one or more of a fibrous capsule, subsynovium, synovial membrane, synovium, joint cavity, synovial fluid, articular cartilage, subchondral bone, and/or ligaments. A pressure-exerting element for applying pressure to an elastic body is described in Gavriely, et al., U.S. 2009/0155341 A1 entitled "Medical Device and A Method for Applying A Biochemically Active Material On One or More Body Parts" published Jun. 18, 2009 which is incorporated herein by reference. The microneedles are connected to a reservoir containing naproxen (NAPROSYN®), available from Roche Laboratories, Nutley, N.J.) to provide anti-inflammatory medicament for repeated local delivery to the knee joint. Local delivery of concentrated naproxen solutions, e.g., approximately 25-200 mg/ml, may be achieved while avoiding potential adverse reactions. Elimination of naproxen from synovial fluid is slow, and appreciable drug concentrations may still be measurable after 24 hours. During once daily dosing of naproxen sodium, naproxen should accumulate in synovial fluid, a steady-state being achieved within a week of treatment. The predicted accumulation ratio based on trough concentration is 2.4. See, e.g., Bruno et al., Br. J. clin. Pharmac., 26: 41-44, 1988, which is incorporated herein by reference.

The hip sheath device contains a medicament applicator comprised of hollow microneedle arrays that are connected to a reservoir containing therapeutic medicaments. Hollow microneedle arrays may be fabricated using microfabrication technology adapted from the microelectronics industry. For example silicon hollow microneedle arrays may be fabricated by etching holes through silicon wafers using deep reactive ion etching and then etching microneedles around the holes. See, e.g., McAllister et al., Proc. Natl. Acad. Sci. USA, 100: 13755-13760, 2003 which is incorporated herein by reference. Microneedle arrays (10×10) containing 100 microneedles in an area of 3×3 mm are constructed with conical microneedles approximately 150 µm in length; with a base diameter of approximately 80 µm and a tip with approximately a 1 µm radius of curvature. Hollow microneedles with diameters between 35 µm and 300 µm and lengths between 150 µm and 1000 µm may be fabricated as shown by McAllister et al., Ibid. Alternatively hollow microneedles may be fabricated from metals, e.g., Ni or NiFe, or polymers, e.g., polyglycolic acid and poly lactic acid, by using micromolds or by electroplating polymer microneedles with nickel as shown by McAllister et al., Ibid. Hollow microneedle arrays may be connected via a manifold to a mini-pump, solenoid valve actuators and to a reservoir containing medicaments. Mini-pumps and solenoid valves are available from Parker-Hannifin, Precision Fluidics Division, Hollis, N.H. The applicator comprised of hollow microneedle arrays, solenoid valve actuators, a minipump and a reservoir is embedded in the hip sheath bandage device with the hollow microneedles facing the stratum corneum overlaying the hip joint. Multiple medicament microneedle arrays may be supported by the hip bandage device to align with different aspects of the hip joint, e.g., anterior, posterior, lateral, medial, superior, inferior.

A hip sheath device may contain sensors to monitor the ambulatory movements of the patient and to actuate the applicator. The sensors may transmit information to the patient, healthcare workers and caregivers. For example, a wearable, hip-mounted movement monitor may be comprised of a tri-axial accelerometer and a microcontroller with micro-circuitry and software as shown by Karantonis, et al., IEEE Trans. Info. Tech. Biomed. 10: 156-167, 2006 which is incorporated herein by reference. The triaxial accelerometer may be comprised of two orthogonally mounted dual axis accelerometers, e.g., MXR7210GL, available from MEMSIC, Inc., North Andover, Mass. A microcontroller, e.g., MSP430F149 available from Texas Instruments, Dallas, Tex., samples output signals from the accelerometers and the data are subject to a classification algorithm embedded in flash memory of the microcontroller. See Karantonis et al., Ibid. for details of the microcontroller and the movement classification algorithm. A movement sensor may distinguish between periods of activity and rest, recognize postural orientation, detect walking and provide an estimate of metabolic energy expenditure. The movement sensor and connected microcontroller may also include predetermined parameters of posture, movement and metabolic energy expenditure that represent thresholds for signaling to actuators, e.g., solenoids, of the applicator to deliver naproxen to the hip joint of the patient. Parameters of posture, movement and energy expenditure may be derived from historical data obtained with the movement sensor from the current patient or from previous patients. The movement sensor and microcontroller may transmit data on movement, posture, and energy expenditure to the patient, healthcare workers, and caregivers as well as data on the dosing and scheduling of naproxen delivery.

The hip sheath device with a medicament applicator and motion sensors has a power source and micro-circuitry to control the dose and schedule of naproxen delivered to the hip joint. A lithium battery may provide electric current to drive solenoid actuator valves and a minipump which are connected to a therapeutic medicament reservoir and microneedle arrays. Delivery of naproxen may be manually controlled by flipping a switch which provides electric current to the applicator. This may be done "as needed" for pain and stiffness. The dose of naproxen delivered may be determined by the concentration of naproxen in the reservoir and the duration of the electric current. Micro-circuitry may monitor the total dose of naproxen delivered within 24 hours and control drug delivery to prevent exceeding the maximum recommended dose. The hip sheath device may also have micro-circuitry including a timer that allows the patient or a healthcare worker to program a dose and schedule of naproxen delivery. The dosing schedule may span hours, days, weeks, or months. The micro-circuitry can record and store total dosage and/or dosage within a fixed time period of hours, days, weeks, or months. The hip sheath device may transmit information including drug dosage, schedule, and drug consumption to a computer network system that is accessible by the patient, the patient's family, healthcare providers, insurance companies, regulatory authorities and/or public health officials.

Example 4

A Glove Device Comprised of High Speed Microjet Applicators Delivers Naproxen (Naprosyn®) in a Thixotropic Medium into the Hand and Wrist Joints of a Patient with Osteoarthritis A device is provided to treat a patient with an arthritic hand and wrist. The device is a glove that is worn on the hand and delivers high local concentrations of an anti-inflammatory drug to the hand and wrist using microjets that are driven by piezoelectric actuators. The patient who has chronic pain and stiffness in his hand and wrist joints is clinically diagnosed to have moderate osteoarthritis as confirmed by radiography. To reduce pain and stiffness a glove device is worn to contact the affected hand and wrist and designed to substantially align multiple embedded microjets with the contours and joints of the hand and wrist. The multiple embedded microjets are configured to provide transdermal delivery of highly concentrated therapeutic medicaments localized to the hand and wrist joints and may effectively deliver the therapeutic medicaments to tissues of the hand and wrist joints including one or more of a fibrous capsule, subsynovium, synovial membrane, synovium, joint cavity, synovial fluid, articular cartilage, subchondral bone, or ligament without risk of adverse reactions associated with oral systemic medicament. Glove devices are designed to fit right hands or alternatively left hands in sizes ranging from small to large. For example, hands may range between approximately 154.51 mm-214.9 mm in length, and 71.62 mm-119.06 mm in breadth. See Mandahawi et al., *Int. J. Indust. Ergon.* 38: 966-976, 2008, which is incorporated herein by reference. A glove device substantially aligns the microjets to deliver naproxen to one or to multiple joints of the hand and wrist including the interphalangial articulations, metacarpophalangeal joints, intercarpal articulations and the radiocarpal joint. For additional detail see Gray, *Gray's Anatomy: The Anatomical Basis of Medicine and Surgery*, (38th ed., Churchill Livingstone 1995; ISBN: 0443045607). The microjets are connected to a reservoir containing naproxen (NAPROSYN®), available from Roche Laboratories, Nutley, N.J.) to provide anti-inflammatory medicament for repeated local delivery to the hand and wrist joints. Local delivery of concentrated naproxen solutions (e.g., approximately 25-200 mg/ml) may be achieved while avoiding potential adverse reactions. Potential adverse reactions associated with systemic oral naproxen include one or more of gastrointestinal bleeding, gastrointestinal ulceration/perforation, myocardial infarction, stroke, thromboembolism, congestive heart failure, renal papillary necrosis, nephrotoxicity, or hepatotoxicity. See *Physician's Desk Reference*, $63^{rd}$ ed. Thomson Healthcare, Montvale, N.J., 2009; ISSN: 0093-4461, which is incorporated herein by reference. For example, a single microjet activated with a piezoelectric crystal may transdermally deliver approximately 28 mg of a drug in a day from a reservoir with a 20 mg/ml solution of drug. See, e.g., Arora et al., *Proc. Natl. Acad. Sci. USA*, 104: 4255-4260, 2007, which is incorporated herein by reference. Localized dosing of a concentrated naproxen suspension, e.g., NAPROSYN® suspension, 25 mg/ml, (available from Roche Laboratories, Nutley, N.J.) at hand joints and wrist joints may be accomplished with a glove device containing multiple embedded microjets actuated by piezoelectric actuators that are controlled electronically using a lithium battery as a source of power. Piezoelectric crystal actuators expand when electronically activated to drive small liquid volumes, e.g., 10-15 nanoliters, through a microjet at high velocity, e.g., greater than 100 meter/sec. See, e.g., U.S. 20080091139 entitled, "Methods, Devices and Kits for Microjet Drug Delivery" published Apr., 17, 2008; and Arora et al., Ibid. The rate of drug delivery may be modulated by varying the electronic signal frequency. For example, electronic signals to piezoelectronic crystals at 10 Hz actuate microjets ten times faster than 1 Hz signals and increase the rate of drug delivery by ten-fold. See, e.g., Arora et al., Ibid. In addition, the dosing of naproxen may also be controlled by variation of the drug concentration in the reservoir. Drug solutions or suspensions may be approximately 2 mg/ml, up to approximately 20 mg/ml, or up to approximately 200 mg/ml.

A glove device with an applicator comprised of microjets to deliver naproxen at high concentration into joints of the hand and wrist may contain naproxen in combination with a thixotropic medium which promotes delivery of naproxen to joint tissues and the synovial cavity. Thixotropic media, e.g., alpha-cyclodextrin, carteolol hydrochloride, are useful for pharmaceutical applications because thixotropic pharmaceutical compositions display reduced viscosity when subjected to shear stress such as high velocity flow through a microjet. The use of thixotropic media for delivery of pharmaceuticals is described in U.S. Pat. No. 6,143,329 entitled "Aqueous-based pharmaceutical composition" issued to Kim on Nov. 7, 2000, which is incorporated herein by reference. For example, parenteral injection of a thixotropic suspension of a pharmaceutical mixed with a small amount of polysorbate 80 (available from Mallincrodt Baker, Inc., Phillipsburg, N.J.) in water is decomposed to a liquid during passage through a medicament applicator, but regains a hydrogel structure and forms cohesive depots in the body. See Lee et al., *J. Contr. Rel.* 136: 88-98, 2009 which is incorporated herein by reference. Semisolid formulations comprised of solid lipid nanoparticles loaded with pharmaceuticals and CARBOPOL® 934 poly(acrylic acid) microgel have thixotropic properties and may be used as topical particulate carriers for antifungal agents. See Lee et al., Ibid. A particulate thixotropic medium combined with naproxen and co-delivered at high velocity to wrist joint tissues may achieve increased penetration of epidermal tissue, fibrous capsule, subsynovial tissue and synovial membrane. Moreover, the properties of the thixotropic medium will lead to formation and deposition of a viscous liquid or hydrogel solution containing naproxen onto wrist joint tissues and into the wrist joint synovial cavity.

The glove device may be worn throughout the day and activated as needed by the patient via an electronic switch that controls the piezoelectric actuators driving multiple microjets. For example an electronic switch on the glove device may be turned on voluntarily by the patient "as needed" in response to pain and stiffness. Micro-circuitry, including a timer in the glove device may determine the duration of drug delivery (and therefore dose) following activation of the device. Alternatively, the glove device with micro-circuitry may be programmed to periodically deliver naproxen transdermally throughout the day and night on a predetermined dose and schedule as determined by the patient or the patient's physician with no need for manual activation.

Example 5

A Patch Device with Embedded Microjets and Sensors to Monitor Movement and Piezoelectric Actuators Configured to Deliver Naproxen (e.g., Naprosyn®) to an Arthritic Finger Joints at High Local Concentrations in a Time Dependent Manner A device is provided to treat a patient with one or more arthritic finger joints. The device is a patch that is worn on the affected joints and delivers high local concentrations of an anti-inflammatory drug to the one or more finger joints using microjets that are driven by piezoelectric actuators. The device also contains sensors to monitor the gait of the patient and to signal the applicator to deliver an anti-inflammatory, naproxen. The patient who has chronic pain and stiffness in a one or more joints of the hand is clinically diagnosed to have moderate osteoarthritis as confirmed by radiography. To reduce pain and stiffness a patch device is placed in contact with the affected joints of the hand and positioned to substantially align multiple embedded microjets with one or more of the superior, inferior, lateral, medial, posterior or anterior aspects of the one or more finger joints as well as sensors to monitor the patient's gait. The patch device also has sensors to monitor the arthritic patient's gait. A sensor to monitor gait is described by Miesel et al., U.S. 2007/0250134 A1 entitled "Collecting Gait Information for Evaluation and Control of Therapy" published Oct. 25, 2007 which is incorporated herein by reference. The multiple embedded microjets are configured to provide transdermal delivery of highly concentrated therapeutic medicaments localized to the one or more finger joints and may effectively deliver the therapeutic medicaments to tissues of the one or more finger joints without risk of adverse reactions associated with oral systemic medicament. The device can deliver highly concentrated therapeutic medicaments to tissues of the one or more finger joints including one or more of a fibrous capsule, subsynovium, synovial membrane, synovium, joint cavity, synovial fluid, articular cartilage, subchondral bone, or ligament. The patch device may be held in place by VELCRO® strips and alignment of the microjets to the synovial joint is referenced to the location of the one or more finger joints. Alternatively, the patch device may be held in place with adhesive. The patch device with embedded microjets may be aligned to the affected finger joints by visual inspection. The microjets are connected to a reservoir containing naproxen (NAPROSYN®, available from Roche Laboratories, Nutley, N.J.) to provide anti-inflammatory medicament for repeated local delivery to the one or more finger joints. Local delivery of concentrated naproxen solutions (e.g., approximately 25-200 mg/ml) may be achieved while avoiding potential adverse reactions. For example, a single microjet activated with a piezoelectric crystal may transdermally deliver approximately 28 mg of a drug in a day from a reservoir with a 20 mg/ml solution of drug. See, e.g., Arora et al., *Proc. Natl. Acad. Sci. USA,* 104: 4255-4260, 2007, which is incorporated herein by reference. Localized dosing of a concentrated naproxen suspension (e.g., NAPROSYN® suspension 25 mg/ml, available from Roche Laboratories, Nutley, N.J.) at the one or more finger joints may be accomplished with a patch device containing multiple embedded microjets actuated by piezoelectric actuators that are controlled electronically using a lithium battery as a source of power. Piezoelectric crystal actuators expand when electronically activated to drive small liquid volumes (e.g., 10-15 nanoliters) through a microjet at high velocity (greater than 100 meter/sec). The high velocity (v>100 m/s) of microjets allows their entry into the skin, whereas the small jet diameters (50-100 μm) and extremely small volumes (2-15 nanoliters) limit the penetration depth (~200 μm) See, e.g., U.S. 2008/0091139 entitled "Methods, Devices and Kits for Microjet Drug Delivery" published Apr., 17, 2008; and Arora et al., Ibid. The rate of drug delivery may be modulated by varying the electronic signal frequency. For example, electronic signals to piezoelectronic crystals at 10 Hz actuate microjets ten times faster than 1 Hz signals and increase the rate of drug delivery by ten-fold. See, e.g., Arora et al., Ibid. In addition, the dosing of naproxen may also be controlled by variation of the drug concentration in the reservoir. Drug solutions or suspensions may be approximately 2 mg/ml, up to approximately 20 mg/ml, or up to approximately 200 mg/ml.

A patch device may contain sensors to monitor the movements of the hands and fingers of the patient and to actuate the applicator. The sensors may transmit information to the patient, healthcare workers and caregivers. For example, a wearable, hand-mounted movement monitor may be comprised of a triaxial accelerometer and a microcontroller with micro-circuitry and software as shown by Karantonis, et al., *IEEE Trans. Info. Tech. Biomed.* 10: 156-167, 2006 which is incorporated herein by reference. The triaxial accelerometer may be comprised of two orthogonally mounted dual axis accelerometers, e.g., MXR7210GL, available from MEMSIC, Inc., North Andover, Mass. A microcontroller, e.g., MSP430F149 available from Texas Instruments, Dallas, Tex., samples output signals from the accelerometers and the data are subject to a classification algorithm embedded in flash memory of the microcontroller. See Karantonis et al., Ibid. for details of the microcontroller and the movement classification algorithm. A movement sensor may distinguish between periods of activity and rest, recognize postural orientation, detect hand movement and provide an estimate of metabolic energy expenditure. The movement sensor and connected microcontroller may also include predetermined parameters of posture, movement and metabolic energy expenditure that represent thresholds for signaling to actuators, e.g., solenoids, of the applicator to deliver naproxen to the one or more finger joints of the patient. Parameters of posture, movement and energy expenditure may be derived from historical data obtained with the movement sensor from the current patient or from previous patients. The movement sensor and microcontroller may transmit data on movement, posture, and energy expenditure to the patient, healthcare workers, and caregivers as well as data on the dosing and scheduling of naproxen delivery.

The patch device with a medicament applicator and motion sensors has a power source and micro-circuitry to control the dose and schedule of naproxen delivered to the one or more finger joints. A lithium battery may provide electric current to drive solenoid actuator valves and a minipump which are connected to a therapeutic medicament reservoir and microneedle arrays. Delivery of naproxen may be manually controlled by flipping a switch which provides electric current to the applicator. This may be done "as needed" for pain and stiffness. The dose of naproxen delivered may be determined by the concentration of naproxen in the reservoir and the duration of the electric current. Micro-circuitry may monitor the total dose of naproxen delivered within 24 hours and control drug delivery to prevent exceeding the maximum recommended dose. The patch device may also have micro-circuitry including a timer that allows the patient or a healthcare worker to program a dose and schedule of naproxen delivery. The dosing schedule may span hours, days, weeks, or months. The micro-circuitry can record and store total dosage and/or dosage within a fixed time period of hours, days, weeks, or months. The patch device may transmit information including drug dosage, schedule, and drug consumption to a computer network system that is accessible by the patient, the patient's family, healthcare providers, insurance companies, regulatory authorities and/or public health officials.

Example 6

A Desktop Device with a Medicament Applicator and Sensors to Identify, Locate and Deliver Diclofenac Sodium (e.g., Voltaren® to Inflamed Joints of the Wrists and Hands of a Patient with Rheumatoid Arthritis A device is provided to treat a patient with arthritic hands and wrists. The device is a desktop unit including an enclosure that surrounds one or more hands and wrists and delivers high local concentrations of medicaments to the hands and wrists using microjets that are driven by piezoelectric actuators. The patient who has symmetric polyarthritis with swelling of the hand joints displays morning stiffness and tests positive for rheumatoid factor is clinically diagnosed to have rheumatoid arthritis. To reduce pain and stiffness in one or more joint tissues and to modify the disease process in a mammalian subject, a desktop device with sensors is used to detect inflamed joints and to align multiple embedded microjets with the inflamed joints of the hand and wrist. The patient's hand is inserted into the desktop device and the hand is imaged within the desktop device, e.g., with ultrasound, to locate the position of inflamed joints in the hand and wrist. The multiple embedded microjets are aligned with the joint tissues of the hand, and the multiple embedded microjets are configured to provide transdermal delivery of highly concentrated therapeutic medicaments localized to the hand and wrist joints. The device including multiple embedded microjets aligned to the one or more joint tissues may effectively deliver the therapeutic medicaments to tissues of the hand and wrist joints including one or more of a fibrous capsule, subsynovium, synovial membrane, synovium, joint cavity, synovial fluid, articular cartilage, subchondral bone, or ligament without risk of adverse reactions that are associated with oral systemic medicaments for treatment of joint disease.

A desktop device with openings for insertion of a right and left hand contains multiple microjets supported by glove-like templates in positions corresponding approximately to the 14 joints present on each hand and to the wrist joint. The device openings are designed with glove-like templates that immobilize a right hand and a left hand of the patient in sizes ranging from small to large. For example, hands may range between approximately 154.51 mm-214.9 mm in length, and 71.62 mm-119.06 mm in breadth. See Mandahawi et al., *Int. J. Indust. Ergon.* 38: 966-976, 2008, which is incorporated herein by reference. Ultrasound sensors present in the desktop unit detect the joints of the hands and wrist and transmit signals locating multiple microjets proximal to the joints of the hand and wrist including one or more of the interphalangial articulations, metacarpophalangeal joints, intercarpal articulations and the radiocarpal joint. Positioning systems for ultrasound can be used in the desktop device. See, e.g., U.S. Pat. No. 7,128,711 entitled "Positioning systems and methods for guided ultrasound therapy systems" issued to Medan et al on Oct. 31, 2006, which is incorporated by reference herein. Ultrasound sensors can be used that are suitable for three dimensional medical imaging. See e.g., Huang et al., *Applied Physics Letters* 92: 193509, 2008, which is incorporated herein by reference. Ultrasound sound images are analyzed by computer software to identify inflamed hand and wrist joints. Computer analyses may be confirmed by a physician or an imaging expert. The desktop device and associated computer system can target inflamed joints for treatment and can actuate the corresponding microjets to deliver anti-inflammatory and anti-rheumatic medicaments to the one or more joint tissues of the patient. Moreover the computer system records the dose and schedule of medicaments delivered to each joint of the hand and wrist, and the information is used along with the patient's medical history to plan future treatment plans.

The microjets are connected to a reservoir containing diclofenac (VOLTAREN®, available from Novartis Pharmaceuticals Corp., East Hanover, N.J.) and methotrexate, e.g., TREXALL® available from Teva Pharmaceuticals USA, North Wales, Pa., to provide anti-inflammatory medicament and a disease-modifying anti-rheumatic drug respectively for local delivery to the hand and wrist joints. Local delivery of concentrated diclofenac sodium solutions, e.g., approximately 25-200 mg/ml, and concentrated methotrexate solutions, e.g., 75-250 mg/ml, may be achieved while avoiding potential systemic adverse reactions and drug interactions. Local delivery of concentrated diclofenac sodium and methotrexate solutions with microjets provides high doses of medicaments localized to one or more joint tissues without the likelihood of adverse events and drug interactions that can be associated with systemic oral medicaments. For example, a single microjet activated with a piezoelectric crystal may transdermally deliver approximately 28 mg of a drug in a day from a reservoir with a 20 mg/ml solution of drug. See, e.g., Arora et al., *Proc. Natl. Acad. Sci. USA*, 104: 4255-4260, 2007, which is incorporated herein by reference. Localized dosing of a concentrated diclofenac (VOLTAREN®, available from Novartis Pharmaceuticals Corp., East Hanover, N.J.) at hand and wrist joints may be accomplished with a desktop device containing multiple embedded microjets actuated by piezoelectric actuators that are controlled electronically using a lithium battery as a source of power. Piezoelectric crystal actuators expand when electronically activated to drive small liquid volumes, e.g., 10-15 nanoliters, through a microjet at high velocity, greater than 100 meter/sec. See, e.g., U.S. 20080091139 entitled, "Methods, Devices and Kits for Microjet Drug Delivery" published Apr., 17, 2008; and Arora et al., Ibid. The rate of drug delivery may be modulated by varying the electronic signal frequency. For example, electronic signals to piezoelectronic crystals at 10 Hz actuate microjets ten times faster than 1 Hz signals and increase the rate of drug delivery by ten-fold. See, e.g., Arora et al., Ibid. In addition, the dosing of diclofenac sodium may also be controlled by variation of the drug concentration in the reservoir. Drug solutions or suspensions may be approximately 2 mg/ml, up to approximately 20 mg/ml, or up to approximately 200 mg/ml.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an surgeon determines that speed and accuracy are paramount, the surgeon may opt for a mainly hardware and/or firmware vehicle; alternatively, if flexibility is paramount, the surgeon may opt for a mainly software implementation; or, yet again alternatively, the surgeon may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the surgeon, any of which may vary. Those skilled in the art will recognize that optical aspects of implementations will typically employ optically-oriented hardware, software, and or firmware.

In a general sense, the various aspects described herein can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
positioning a device over one or more body contours of a mammalian subject, the one or more body contours at least partially covering one or more joints of articulating bone, wherein the device includes one or more substrates configured to contact the one or more body contours; one or more sensors configured to detect one or more joints exhibiting one or more physiological conditions; one or more microjet applicators supported by the one or more substrates; and a controller configured to respond to the one or more sensors by substantially aligning the one or more microjet applicators with the one or more joints exhibiting the one or more physiological conditions detected by the one or more sensors; and
injecting one or more medicaments to the one or more joint tissues of the mammalian subject using the device.

2. The method of claim 1, wherein the one or more microjet applicators include one or more high speed microjets.

3. The method of claim 2, wherein the high speed microjets are nanoliter-volume pulsed microjets.

4. The method of claim 1, wherein the one or more substrates includes one or more patches or one or more sheaths.

5. The method of claim 4, wherein the one or more sheaths includes a sleeve-shaped article of clothing or a sleeve-shaped body covering.

6. The method of claim 5, wherein the one or more sheaths includes a shirt sleeve, a pant, a leg covering, a stocking, a bandage-like covering, a brace, a knee brace, an elbow brace, an ankle brace, a foot brace, a hand brace, or a spinal brace.

7. The method of claim 6, wherein the one or more substrates is attached to the one or more body contours by glue, suction, or suture.

8. The method of claim 1, wherein the one or more joint tissues includes one or more of a fibrous capsule, subsynovium, synovial membrane, synovium, joint cavity, synovial fluid, articular cartilage, subchondral bone, or ligament.

9. The method of claim 1, wherein the one or more joints includes a synovial joint, cartilaginous joint, or fibrous joint.

10. The method of claim 1, wherein the one or more sensors are configured to detect movement of the one or more body contours.

11. The method of claim 10, wherein the one or more sensors are configured to monitor joint movement, body movement, or gait of the mammalian subject.

12. The method of claim 10, wherein the one or more sensors are configured to monitor posture of the mammalian subject.

13. The method of claim 1, wherein the one or more sensors are configured to detect tissue swelling, tissue pressure, tissue color, tissue temperature, environmental temperature, electrical property of tissue, optical property of tissue, perspiration, or presence of an analyte.

14. The method of claim 13, wherein the analyte includes an inflammatory marker, antibody, or cytokine.

15. The method of claim 1, wherein the one or more sensors are configured to determine quality of location or quality of contact placement of the one or more sheaths on the one or more body contours.

16. The method of claim 1, wherein the controller is configured to control release of the one or more medicaments from the one or more applicators.

17. The method of claim 16, wherein the controller is configured to control a timed-release dosage of the one or more medicaments.

18. The method of claim 16, wherein the controller is configured to report quantity and frequency of dosage of the one or more medicaments.

19. The method of claim 16, wherein the controller is configured to control a maximum dosage of the one or more medicaments for a time period.

20. The method of claim 1, wherein the one or more sensors are configured to detect one or more physiological conditions at one or more of the one or more joints and the controller is configured to control release of the one or more medicaments at others of the one or more joints of the mammalian subject.

21. The method of claim 20, wherein the one or more sensors are configured to detect movement of the one or more body contours.

22. The method of claim 1, wherein the one or more applicators further include tissue permeabilization components including one or more of electronics, ultrasonics, chemical permeation enhancer, iontophoresis, microdialysis, ultrafiltration, electromagnetic, electroosmosis, sonophoresis, microdialysis, suction, electroporation, thermal poration, microporation, heating component, or laser.

23. The method of claim 1, further including providing a component for transient mechanical/electrical acceleration of the one or more medicaments from the microjets.

24. The method of claim 23, wherein the component for transient mechanical/electrical acceleration includes a fluid displacement actuator configured as one or more piezoelectric actuators, one or more springs, one or more solenoids, one or more magnets, one or more motors, or one or more compressed gas actuators.

25. The method of claim 23, wherein the component for mechanical/electrical acceleration applies concentration gradients of the one or more medicaments in a time-dependent manner.

26. The method of claim 1, wherein the one or more medicaments includes steroids, corticosteroids, analgesics, COX-2 inhibitors, or NSAID.

27. The method of claim 1, further including providing a pharmaceutical composition including the one or more medicaments in a thixotropic medium.

28. The method of claim 1, wherein the one or more microjet applicators are configured to apply the one or more medicaments in a time-dependent manner.

29. The method of claim 28, wherein the one or more microjet applicators are configured to apply the one or more medicaments in concentration gradients in the time-dependent manner.

* * * * *